(12) United States Patent
Yoon et al.

(10) Patent No.: US 12,125,576 B2
(45) Date of Patent: Oct. 22, 2024

(54) METHOD AND SYSTEM FOR PROVIDING EXERCISE THERAPY USING ARTIFICIAL INTELLIGENCE POSTURE ESTIMATION MODEL AND MOTION ANALYSIS MODEL

(71) Applicant: EVEREX, Seoul (KR)

(72) Inventors: Chan Yoon, Seoul (KR); Byung Hoon Kim, Seoul (KR)

(73) Assignee: EVEREX, Seoul (KR)

( * ) Notice: Subject to any disclaimer, the term of this patent is extended or adjusted under 35 U.S.C. 154(b) by 0 days.

(21) Appl. No.: 18/531,375

(22) Filed: Dec. 6, 2023

(65) Prior Publication Data
US 2024/0203557 A1 Jun. 20, 2024

Related U.S. Application Data

(63) Continuation of application No. PCT/KR2023/003805, filed on Mar. 22, 2023.

(30) Foreign Application Priority Data

Dec. 15, 2022 (KR) .................. 10-2022-0176240
Dec. 15, 2022 (KR) .................. 10-2022-0176241

(51) Int. Cl.
*G16H 20/30* (2018.01)
*A61B 5/11* (2006.01)
(Continued)

(52) U.S. Cl.
CPC .......... *G16H 20/30* (2018.01); *A61B 5/1128* (2013.01); *G16H 10/60* (2018.01); *G16H 30/40* (2018.01); *G16H 40/67* (2018.01); *G16H 50/20* (2018.01)

(58) Field of Classification Search
CPC ........ G16H 20/30; G16H 30/40; G16H 40/67; G16H 50/20; G16H 10/60; A61B 5/1128
(Continued)

(56) References Cited

U.S. PATENT DOCUMENTS 11,273,343 B2 * 3/2022 Augustin ........... A63B 21/0724

FOREIGN PATENT DOCUMENTS

JP 2021-514512 A 6/2021
KR 10-2015-0096550 A 8/2015
(Continued)

OTHER PUBLICATIONS

Ha Dae Su, "Systems and Methods for Analyzing Line-and-face Recognition-based Motion Posture", KR 102340519 B1, Date published: Dec. 20, 2021) (Year: 2021).*
(Continued)

*Primary Examiner* — John H Le
(74) *Attorney, Agent, or Firm* — Bridgeway IP Law Group, PLLC; Jihun Kim

(57) ABSTRACT

A method of providing exercise therapy using an artificial intelligence motion analysis model comprises: receiving, from a doctor terminal, prescription information related to exercise for a patient; allocating, to an account of the patient, based on the prescription information, an exercise plan including at least one prescribed exercise; receiving, from a patient terminal, an exercise image in which an exercise according to the prescribed exercise is photographed; extracting, from the exercise image including a subject of the patient, a keypoint corresponding to each of a plurality of preset joint points, using an artificial intelligence posture estimation model trained based on a training data set; and analyzing, using an artificial intelligence motion analysis model, a relative positional relationship between the keypoints, and analyzing, based on the analysis of the positional relationship, an exercise motion of the patient for the prescribed exercise.

8 Claims, 21 Drawing Sheets

(51) Int. Cl.
*G16H 10/60* (2018.01)
*G16H 30/40* (2018.01)
*G16H 40/67* (2018.01)
*G16H 50/20* (2018.01)

(58) Field of Classification Search
USPC .......................................................... 702/150
See application file for complete search history.

(56) References Cited

FOREIGN PATENT DOCUMENTS

| | | |
|---|---|---|
| KR | 10-2195512 B1 | 12/2020 |
| KR | 10-2021-0128943 A | 10/2021 |
| KR | 10-2340519 B1 | 12/2021 |
| KR | 10-2355008 B1 | 1/2022 |
| KR | 10-2022-0013347 A | 2/2022 |
| KR | 10-2360284 B1 | 2/2022 |

OTHER PUBLICATIONS

Yanlei Gu et al., "Multi-Person Pose Estimation using an Orientation and Occlusion Aware Deep Learning Network", Sensors 2020 Article, Mar. 12, 2020, 20(6), 1593.

* cited by examiner

FIG. 4B

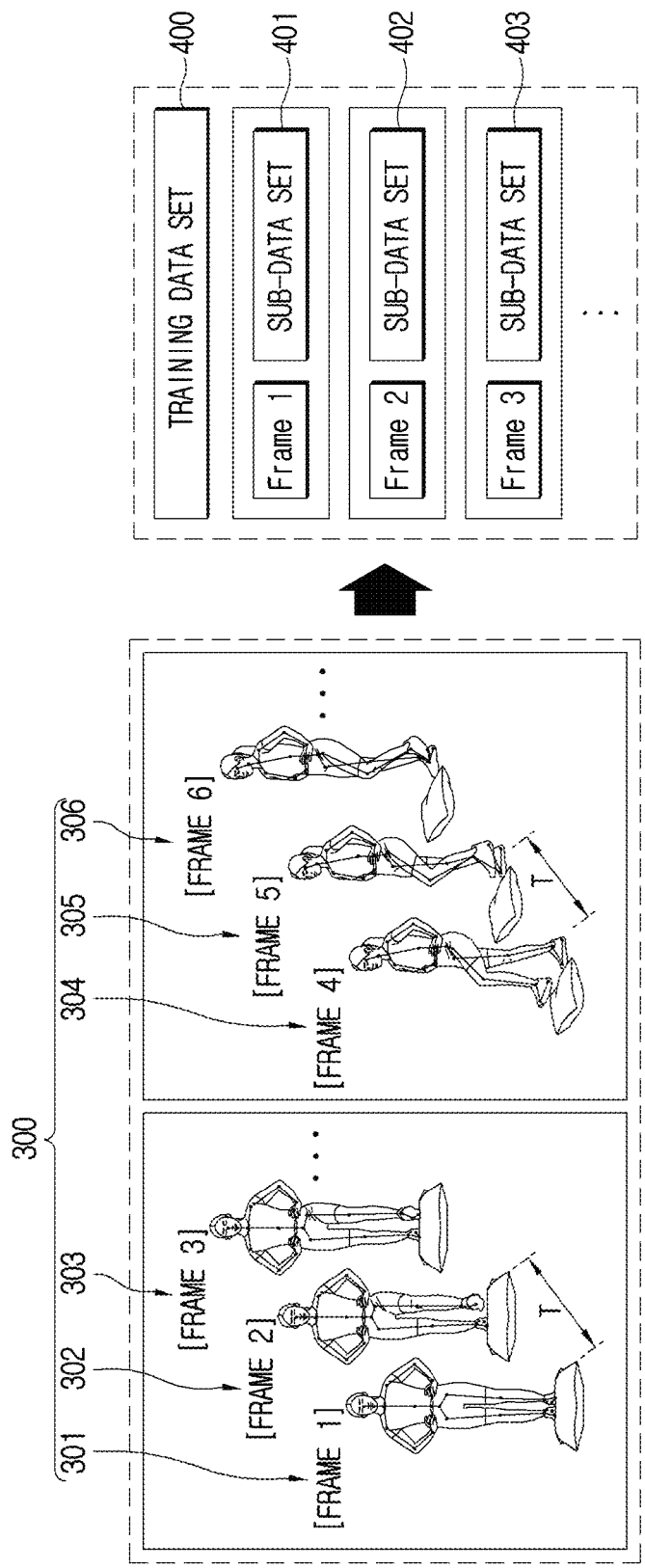

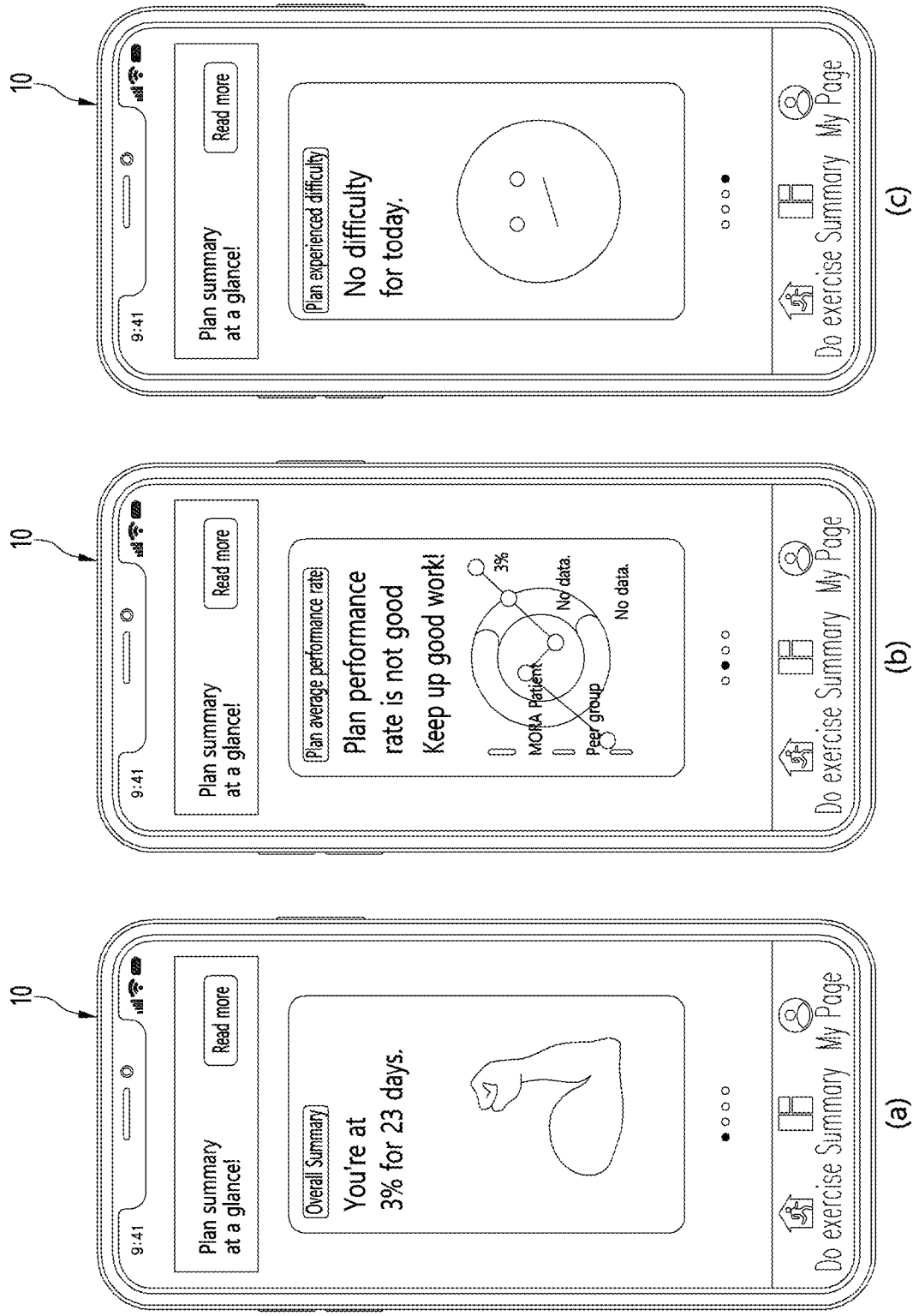

METHOD AND SYSTEM FOR PROVIDING EXERCISE THERAPY USING ARTIFICIAL INTELLIGENCE POSTURE ESTIMATION MODEL AND MOTION ANALYSIS MODEL

CROSS REFERENCE TO RELATED APPLICATION

The application is a Continuation Application of International Application PCT/KR2023/003805 filed on Mar. 22, 2023, which claims priority to Korean Patent Application No. 10-2022-0176240, filed on Dec. 15, 2022, and Korean Patent Application No. 10-2022-0176241, filed on Dec. 15, 2022, the entire contents of which is incorporated herein for all purposes by this reference.

FIELD OF THE INVENTION

The present invention relates to a method and system for providing exercise therapy to a patient using an artificial intelligence posture estimation model and an artificial intelligence motion analysis model specialized for a musculoskeletal disease.

DESCRIPTION OF THE RELATED ART

A musculoskeletal disease is pain or damage to a musculoskeletal system, such as muscles, nerves, tendons, ligaments, bones, and surrounding tissues. The musculoskeletal disease appears in many places in the body, including the neck and back, arms and legs, and more.

According to the World Health Organization (WHO), the economic losses from the musculoskeletal disease are the fourth highest of all diseases, and the musculoskeletal disease is chronic pain that affects not only daily life but also economic activity.

Meanwhile, the principle of treating musculoskeletal disease is to start with the least invasive treatment, which means that non-drug conservative treatments (e.g., exercise therapy and education, cognitive therapy, or relaxation therapy) should be performed first, and then drug and surgical treatments should be considered sequentially.

Treatment guidelines strongly recommend non-drug conservative treatment of musculoskeletal disease, and there is active research, mainly in the United States and Europe, on methods of performing non-drug conservative treatments of musculoskeletal disease.

Meanwhile, as technology has advanced, electronic devices (e.g., smartphones, tablet PCs, etc.) have become more widely available, and thus dependence on the internet for many aspects of daily life has become gradually increasing.

As such, with the development of various technologies, including the Internet, consumption patterns that were previously highly dependent on offline activities have gradually shifted to online, and currently, the consumption centered around the online world has been experiencing exponential growth.

In response to this trend changes, even offline-based fields of industry, such as the healthcare industry, has been commonly providing healthcare services online.

In this regard, in recent years, various healthcare services have been provided online, and patients, i.e., users, have been able to have medical consultations with healthcare providers about their illnesses with just a few clicks on an internet-connected electronic device.

As an example of such technology, Korean Patent No. 10-2195512 discloses a technology related to a server and system that provides an online healthcare platform and provides information on healthcare service provision points to patients online.

In response to this trend, there is a need to provide non-drug conservative treatment of musculoskeletal disease online.

Disclosure

Technical Problem

The present invention relates to a method and system for providing exercise therapy that is capable of providing online-based exercise therapy for a musculoskeletal disease.

In particular, the present invention relates to a method and system for providing exercise therapy that is capable of analyzing an exercise motion of a patient performing a prescribed exercise, based on an exercise image.

In particular, the present invention relates to a method and system for providing exercise therapy that is capable of analyzing an exercise motion of a patient from an exercise image based on an artificial intelligence model specialized for a musculoskeletal disease.

Further, the present invention relates to a method and system for providing exercise therapy that is capable of providing a user environment in which a patient is easily accessible for a treatment of a musculoskeletal disease.

Meanwhile, the present invention relates to a method and system for estimating exercise posture and analyzing an exercise motion that is capable of providing online-based rehabilitation therapy.

More specifically, the present invention relates to a method and system for estimating exercise posture and analyzing an exercise motion, which is capable of analyzing posture related to an exercise motion of a user for rehabilitation based on an exercise image.

In particular, the present invention relates to a method and system for estimating exercise posture and analyzing an exercise motion that enables user-personalized exercise posture estimation.

Further, the present invention relates to a method and system for estimating exercise posture and analyzing an exercise motion that is capable of building a database (DB) used for estimating exercise posture.

Technical Solution

There is provided a method of providing exercise therapy according to the present invention to achieve the above-mentioned objects, the method may include: receiving, from a doctor terminal, prescription information related to exercise for a patient; allocating, to an account of the patient, based on the prescription information, an exercise plan including at least one prescribed exercise; receiving, from a patient terminal, an exercise image in which an exercise according to the prescribed exercise is photographed; extracting, from the exercise image, a keypoint corresponding to each of a plurality of preset joint points, using an artificial intelligence posture estimation model; analyzing, using an artificial intelligence motion analysis model, a relative positional relationship between the keypoints, and analyzing, based on the analysis of the positional relationship, an exercise motion of the patient for the prescribed exercise; and transmitting an analysis result of the exercise motion of the patient to the patient terminal, based on said analysis.

Further, the method may further include: outputting the exercise image to the patient terminal in real time, in conjunction with the exercise image being photographed on the patient terminal; and providing a graphic object corresponding to the extracted keypoint that overlaps an area where a subject corresponding to the patient is positioned in the exercise image, so as to allow the patient to recognize a joint point where an analysis is performed on an exercise motion of the patient.

In an embodiment, in the extracting of the keypoint, a visible joint point of the subject that is visible in the exercise image may be specified among the plurality of preset joint points, and in which the specified visible joint point may be extracted as the keypoint.

In an embodiment, the motion analysis model may predict, based on the training data, an invisible joint point of the subject that is not visible in the exercise image among the plurality of preset joint points, and analyze, based on the visible joint point and the invisible joint point, the exercise motion of the patient.

In this case, the keypoints may include keypoints corresponding to the visible joint point and the invisible joint point.

In an embodiment, the training data may include a first data group in which position information for a training target visible joint point of the subject included in a training target image and a training target invisible joint point estimated based on the visible joint point are sequentially listed, and a second data group including data values representing whether each of the training target visible joint point and the training target invisible joint point is visible.

In this case, a sequence of listing of the data values included in the second data group may have the same sequence as a sequence in which the training target visible joint point and the training target invisible joint point are listed.

In an embodiment, in the analyzing of the exercise motion of the patient, a relative positional relationship between the keypoints may be analyzed based on rule information related to the prescribed exercise, and the exercise motion of the patient may be analyzed by judging whether the relative positional relationship between the keypoints satisfies the rule information.

In an embodiment, visual appearances of the graphic objects overlapping the exercise image may be configured to be different depending on whether the relative positional relationship between the extracted keypoints satisfies the rule information.

In an embodiment, the analysis result of the exercise motion of the patient may include: a first analysis result providing the graphic object corresponding to the keypoint that overlaps the exercise image in real time with a different visual appearance based on the rule information, in a state in which the exercise image is being photographed on the patient terminal; and a second analysis result including an evaluation score of the patient for the prescribed exercise based on a keypoint extracted from each of a plurality of frames constituting the exercise image.

In this case, the first analysis result may be generated by a motion analysis model of an application installed on the patient terminal, in which the second analysis result may be generated on a cloud server in conjunction with the application, and in which both the first analysis result and the second analysis result may be transmitted to the doctor terminal.

Further, there is provided a system for providing exercise therapy according to the present invention, the system may include: a communication unit configured to receive, from a doctor terminal, prescription information related to an exercise for a patient; and a control unit configured to allocate, based on the prescription information, an exercise plan including at least one prescribed exercise, to an account of the patient, in which the control unit may be configured to: receive, from the patient terminal, an exercise image in which an exercise according to the prescribed exercise is photographed; extract a keypoint corresponding to each of a plurality of preset joint points from the exercise image; analyze a relative position relationship between the keypoints through an artificial intelligence behavioral analysis model; analyze an exercise motion of the patient for the prescribed exercise, based on the analysis of the positional relationship; and transmit an analysis result of the exercise motion of the patient to the patient terminal.

Further, there is provided a system for providing exercise therapy, the system may include: a communication unit configured to receive, from a doctor terminal, prescription information related to an exercise for a patient; and a control unit configured to allocate, based on the prescription information, an exercise plan including at least one prescribed exercise, to an account of the patient, in which the control unit may be configured to: receive, from the patient terminal, an exercise image in which an exercise according to the prescribed exercise is photographed; analyze, from the exercise image, an exercise motion of the patient for the prescribed exercise, using an artificial intelligence motion analysis model: and transmit an analysis result of the exercise motion of the patient, to the patient terminal.

Further, there is provided a program executable by one or more processes on an electronic device and stored on a computer-readable recording medium, the program may include instructions for performing of: receiving, from a doctor terminal, prescription information related to exercise for a patient; allocating, to an account of the patient, based on the prescription information, an exercise plan including at least one prescribed exercise; receiving, from a patient terminal, an exercise image in which an exercise according to the prescribed exercise is photographed; extracting, from the exercise image, a keypoint corresponding to each of a plurality of preset joint points; analyzing, using an artificial intelligence motion analysis model, a relative positional relationship between the keypoints, and analyzing, based on the analysis of the positional relationship, an exercise motion of the patient for the prescribed exercise; and transmitting an analysis result of the exercise motion of the patient to the patient terminal, based on said analysis.

There is provided a method of estimating an exercise posture according to the present invention to achieve the above-mentioned objects, the method may include: receiving, from a user terminal, an exercise image; analyzing, based on posture estimation information extracted from a posture estimation model trained using a training data set 400 including position information for a joint point, an exercise motion related to a specific exercise motion of a user included in the exercise image; and providing, based on a completion of the analysis, an exercise motion analysis result of the user related to the specific exercise motion of the user to the user terminal, in which the position information for the joint point included in the training data set may be position information for each of a plurality of predesignated training target joint points among joint points of a subject included in a training target exercise image, and in which the training data set may be configured with data extracted from the training target exercise image.

In an embodiment, the training data set may be configured with a plurality of data groups, corresponding respectively to different information attributes, in which a first data group of the plurality of data groups may include position information on each of the plurality of training target joint points, and in which, in the position information included in the first data group, coordinate information of each of the plurality of predesignated training target joint points in the training target exercise image may be included in a paired form.

In an embodiment, the position information included in the first data group may be defined as different types of information based on whether the plurality of training target joint points are visible in the training target image, and in which the definition of a type for the position information may be determined by data values of data included in a second data group different from the first data group.

In an embodiment, the posture estimation model may, based on the data value included in the second data group, set a training weight for the position information of each of the plurality of training target joint points included in the first data group differently.

In an embodiment, the position information of each of the plurality of training target joint points included in the first data group may be arranged sequentially within the first data group, based on a predefined sequence among the plurality of training target joint points, and in which the data values included in the second data group may be arranged within the second data group in the same sequence as the predefined sequence in which the position information of each of the plurality of training target joint points is arranged, so as to represent whether each of the plurality of training target joint points is visible.

In an embodiment, the training data set may further include a third data group including data values related to a photographing direction for the subject, in which the data values included in the third data group may be configured to have different data values depending on the photographing direction of the subject with respect to a camera that photographs the subject.

In this case, the posture estimation model may be configured to be trained in consideration of the photographing direction of the subject through the training data set having different data values according to the photographing direction of the subject, and in which an exercise motion analysis result of the user may be a result of analyzing a specific exercise motion of the user based on posture estimation information extracted in consideration of the photographing direction of the user included in the exercise image in the posture estimation model.

In an embodiment, the exercise image received from the user terminal and the training target exercise image may correspond to the specific exercise motion having an identical exercise code, and in which the training data set may include a fourth data group including an exercise code matched to the specific exercise motion performed by the subject in the training target exercise image.

Further, the training target exercise image may be a motion image, and in which the training data set may be configured with training data extracted centered on the subject included in the training target exercise image, from each of a plurality of standard frames selected based on a preset standard among a plurality of frames constituting the training target exercise image.

There is provided a system for estimating an exercise posture according to the present invention, the system may include: a posture estimation model configured to extract posture estimation information using a training data set including position information for a joint point; a motion analysis model configured to analyze, using the posture estimation information, an exercise motion related to a specific exercise motion of a user included in an exercise image targeted for analysis; and a service server configured to provide, based on a completion of the analysis, an exercise motion analysis result of the user related to the specific exercise motion of the user to the user terminal, in which the position information for the joint point included in the training data set may be position information of each of a plurality of predesignated training target joint points among joint points of a subject included in the training target exercise image, and in which the training data set may be configured with data extracted from the training target exercise image.

Further, there is provided a program executed by one or more processes on an electronic device and stored on a computer-readable recording medium, the program may include instructions to perform of: receiving, from a user terminal, an exercise image; analyzing, based on posture estimation information extracted from a posture estimation model trained using a training data set including position information for a joint point, an exercise motion related to a specific exercise motion of a user included in the exercise image; and providing, based on a completion of the analysis, an exercise motion analysis result of the user related to the specific exercise motion of the user to the user terminal, in which the position information for the joint point included in the training data set may be position information for each of a plurality of predesignated training target joint points among joint points of a subject included in a training target exercise image, and in which the training data set may be configured with data extracted from the training target exercise image.

Advantageous Effects

As described above, the method and system for providing exercise therapy according to the present invention can receive, from a doctor terminal, prescription information related to an exercise for a patient, and, based on the prescription information, allocate an exercise plan including at least one prescribed exercise to an account of the patient. This allows a doctor to prescribe to a patient, and a patient to be provided with an exercise plan based on the doctor's prescription, even if the doctor and patient do not meet in person for exercise therapy for a musculoskeletal disease, thereby resolving spatial, temporal, and economic constraints on the exercise therapy and increasing accessibility to the exercise therapy.

Further, the method and system for providing exercise therapy according to the present invention can analyze an exercise motion of a user by extracting a keypoint corresponding to each of a plurality of preset joint points from an exercise image to focus on a joint required for exercise therapy of a musculoskeletal disease.

Further, the method and system for providing exercise therapy according to the present invention can analyze an exercise motion related to a specific exercise motion of a user included in an exercise image based on a posture estimation model trained using a training data set including position information for a joint point. Therefore, in the present invention, it is possible to accurately analyze posture of a patient from an exercise image, and in particular, it is possible to improve the quality of healthcare services by obtaining information on a range of motion, alignment state, and deviation state of a joint of the patient.

Further, the method and system for providing exercise therapy according to the present invention, by transmitting an analysis result of an exercise motion of a patient to a patient terminal, the patient can be provided with feedback on an exercise image without having to visit a hospital located at a distance, thereby enhancing an effect of exercise therapy and improving compliance of the patient to exercise.

As described above, the system for estimating exercise posture and analyzing an exercise motion according to the present invention can analyze an exercise motion related to a specific exercise motion of a user included in an exercise image based on a posture estimation model trained using a training data set including position information for a joint point. Therefore, in the present invention, it is possible to accurately analyze an exercise motion of a user from an exercise image, and in particular, it is possible to improve the quality of healthcare services by obtaining information on a range of motion, alignment state, and deviation state of a joint of the user.

Further, the method of estimating exercise posture according to the present invention can provide an exercise motion analysis result of a user related to a specific exercise motion to the user terminal, so that a patient can be provided with rehabilitation therapy without having to visit a hospital located at a distance, thereby making rehabilitation therapy easily accessible, and a healthcare provider can conveniently monitor a rehabilitation exercise of the patient through an electronic device, and provide feedback based on the monitoring, thereby enhancing an effect of exercise therapy of the patient.

BRIEF DESCRIPTION OF THE DRAWINGS

FIGS. 4A and 4B are conceptual views for describing a doctor's prescription.

FIGS. 7, 8A, 8B, 8C, 8D, 8E, and 8F are conceptual views for describing an artificial intelligence posture estimation model.

FIGS. 9A, 9B, and 9C are conceptual views for describing a user environment in which an exercise motion analysis result of a patient is provided.

DETAILED DESCRIPTION OF THE INVENTION

Figure 1:
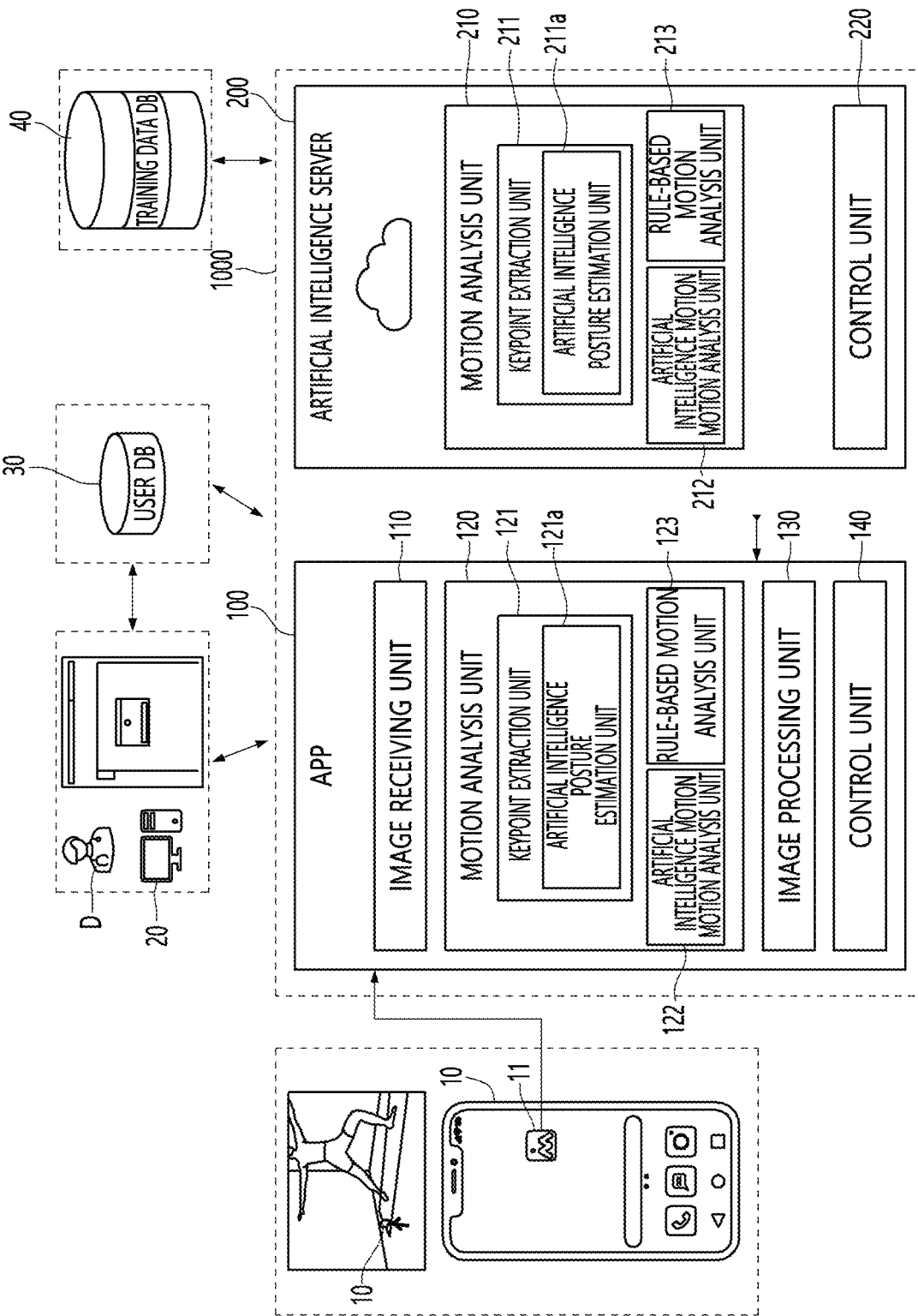
FIG. 1 is a conceptual view for describing a system for providing exercise therapy according to the present invention.

Hereinafter, exemplary embodiments disclosed in the present specification will be described in detail with reference to the accompanying drawings. The same or similar constituent elements are assigned with the same reference numerals regardless of reference numerals, and the repetitive description thereof will be omitted. The suffixes "module", "unit", "part", and "portion" used to describe constituent elements in the following description are used together or interchangeably in order to facilitate the description, but the suffixes themselves do not have distinguishable meanings or functions. In addition, in the description of the exemplary embodiment disclosed in the present specification, the specific descriptions of publicly known related technologies will be omitted when it is determined that the specific descriptions may obscure the subject matter of the exemplary embodiment disclosed in the present specification. In addition, it should be interpreted that the accompanying drawings are provided only to allow those skilled in the art to easily understand the embodiments disclosed in the present specification, and the technical spirit disclosed in the present specification is not limited by the accompanying drawings, and includes all alterations, equivalents, and alternatives that are included in the spirit and the technical scope of the present disclosure.

The terms including ordinal numbers such as "first," "second," and the like may be used to describe various constituent elements, but the constituent elements are not limited by the terms. These terms are used only to distinguish one constituent element from another constituent element.

When one constituent element is described as being "coupled" or "connected" to another constituent element, it should be understood that one constituent element can be coupled or connected directly to another constituent element, and an intervening constituent element can also be present between the constituent elements. When one constituent element is described as being "coupled directly to" or "connected directly to" another constituent element, it should be understood that no intervening constituent element is present between the constituent elements.

Singular expressions include plural expressions unless clearly described as different meanings in the context.

In the present application, it should be understood that terms "including" and "having" are intended to designate the existence of characteristics, numbers, steps, operations, constituent elements, and components described in the specification or a combination thereof, and do not exclude a possibility of the existence or addition of one or more other characteristics, numbers, steps, operations, constituent elements, and components, or a combination thereof in advance.

The present invention is directed to analyzing an exercise motion of a patient included in an exercise image based on the exercise image received from a patient terminal, and providing an analysis result. In particular, the present invention relates to a method of analyzing an exercise motion based on a joint point of a patient using an artificial intelligence model specialized for a musculoskeletal disease.

The present invention is described centered on an exercise motion analysis of a rehabilitation exercise for a musculoskeletal disease, but is not necessarily limited thereto. That is, in the present invention, a motion analysis may include not only an exercise motion, but also an analysis of a variety of motions, such as motions in daily life, motions during stretching, etc.

Meanwhile, the term "exercise motion" described in the present invention refers to a gesture (motion) made in the process of performing an exercise, and may be used interchangeably with the terms "motion", "action", "movement", "gesture", etc. of the body.

Figure 6:
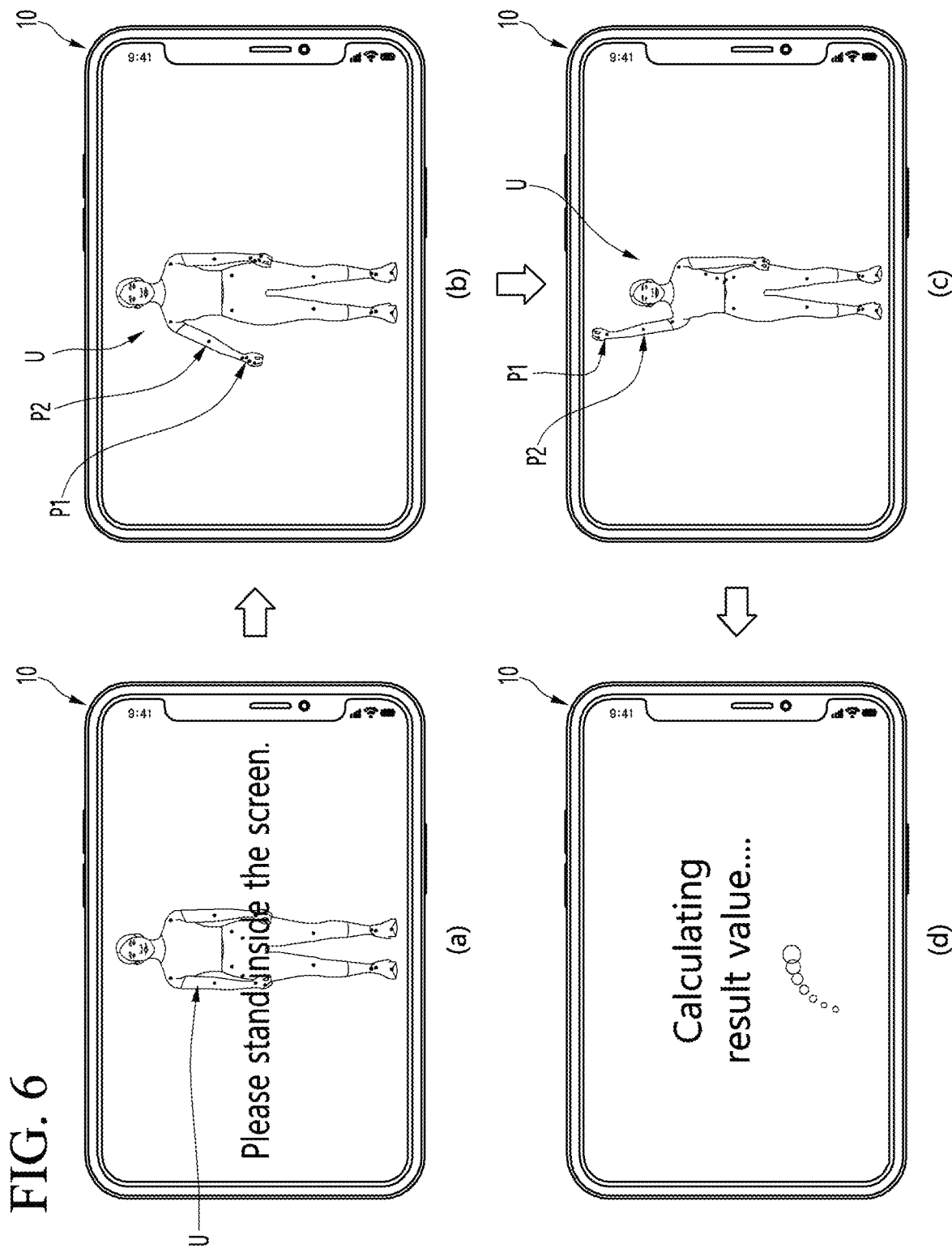

Further, the term "exercise image" refers to an image (or motion image) that photographs a process in which a patient performs an exercise motion, as illustrated in FIG. 6, which may include at least a portion of the body of the patient U.

In the present invention, a patient object included in an exercise image may be described to be referred to as "subject U". In the present invention, the term "subject U" may mean a patient or a portion of the body of the patient who is exercising in the exercise image. In the present invention, the terms "subject" and "patient" may be used interchangeably and may be described by assigning the same reference numeral "U".

Figure 2:
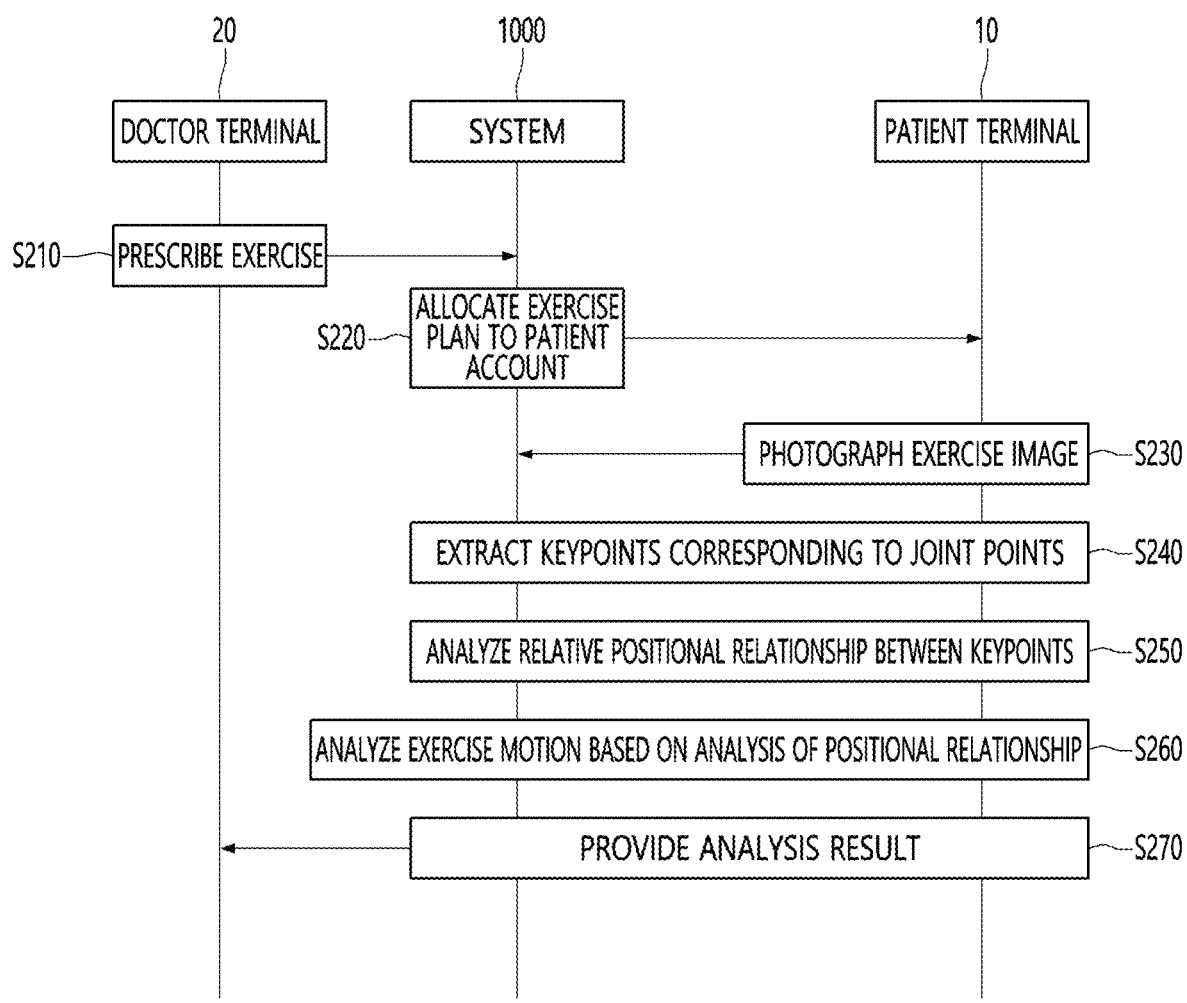
FIGS. 2 and 3 are flowcharts for describing a method of providing exercise therapy according to the present invention.
Figure 3:
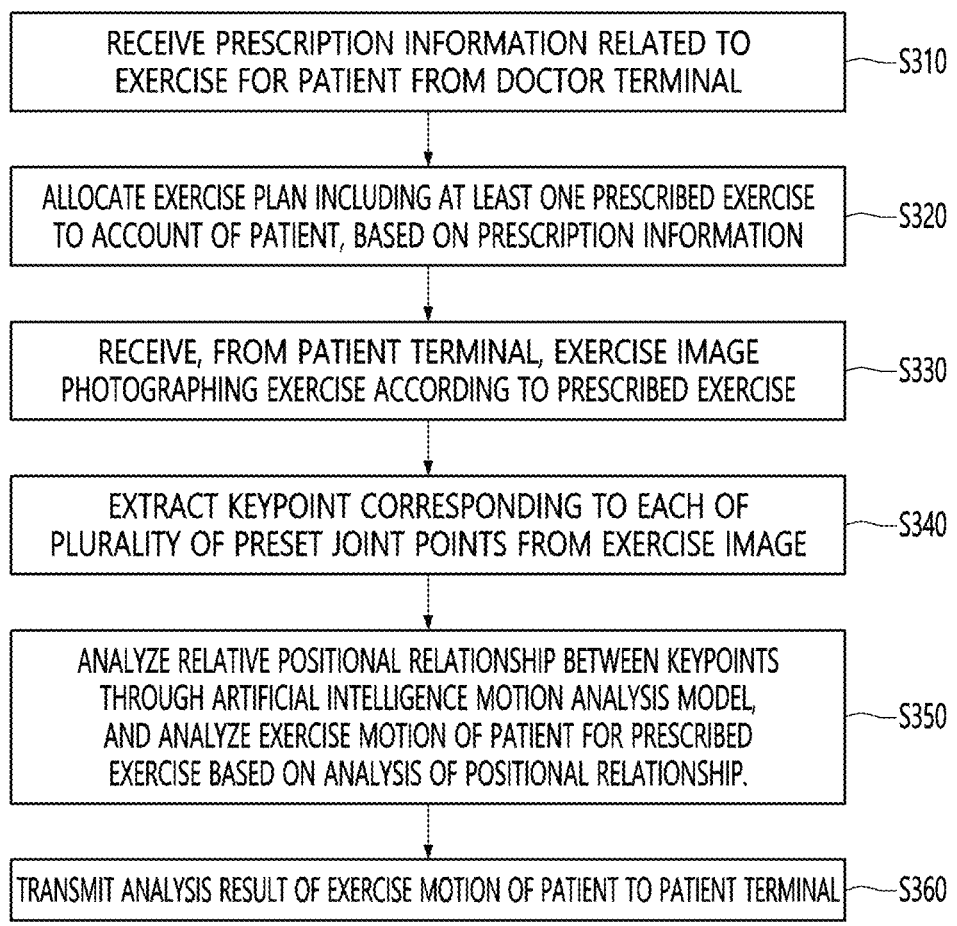
Figure 4A:
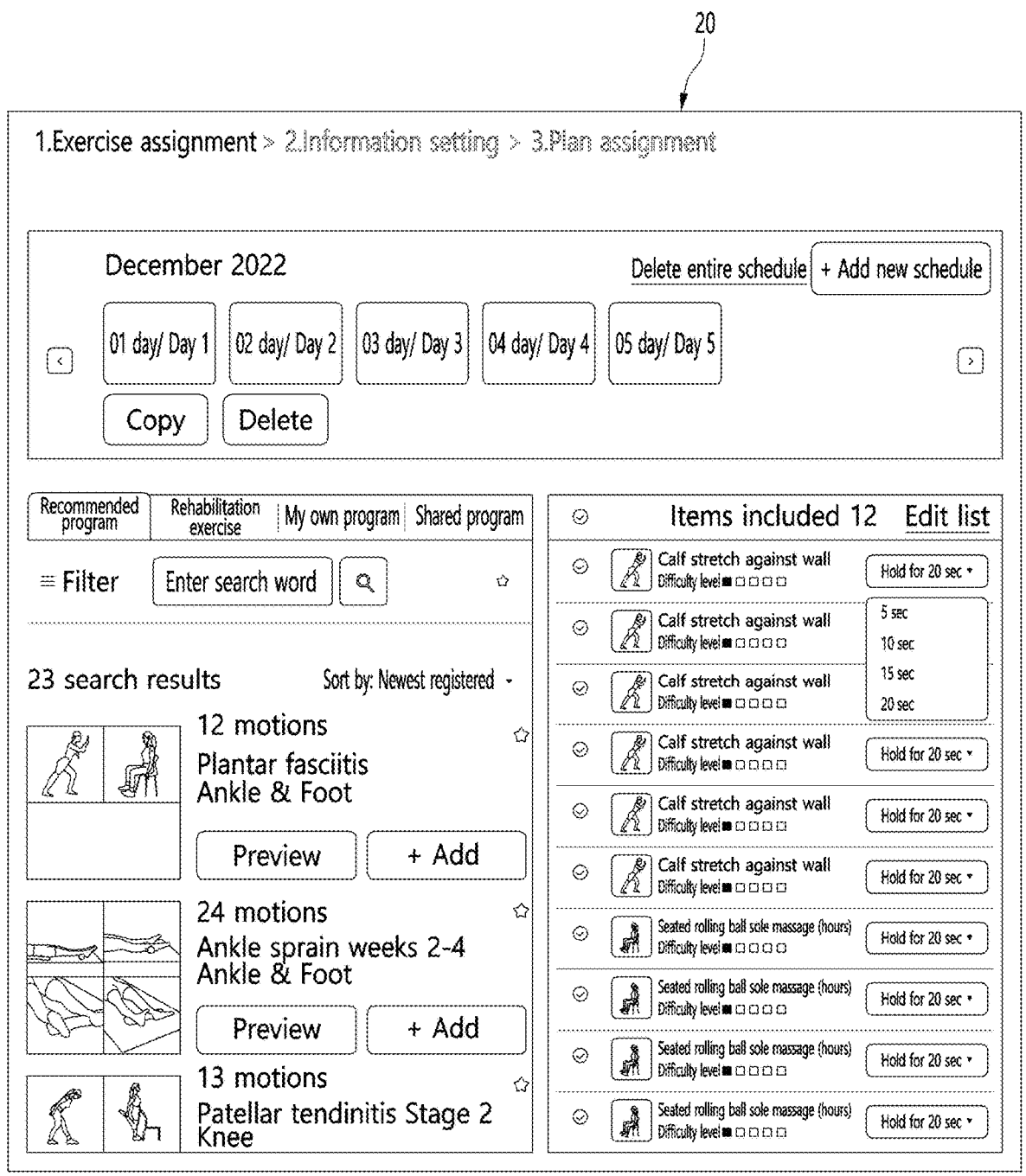
Figure 4B:
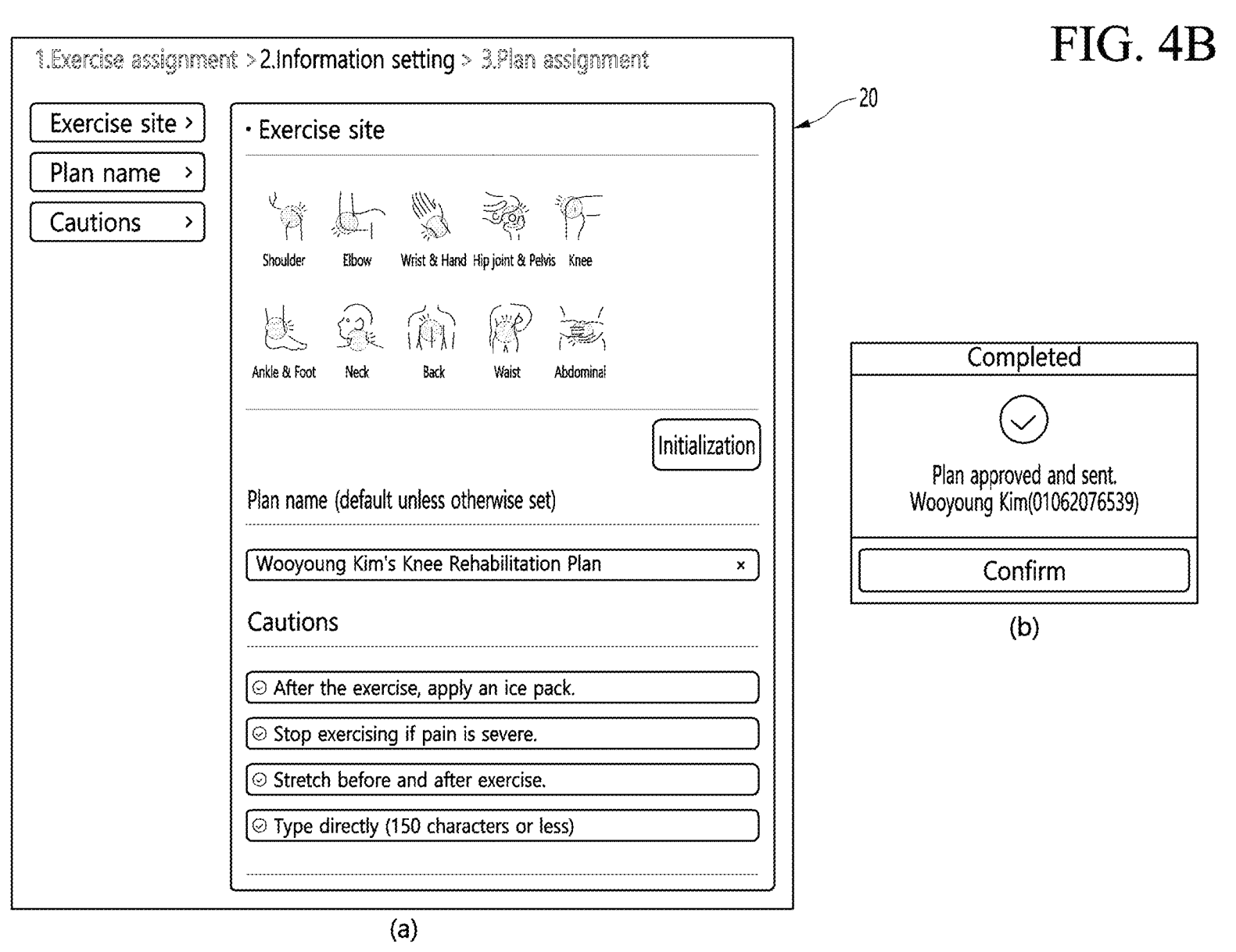
Figure 5:
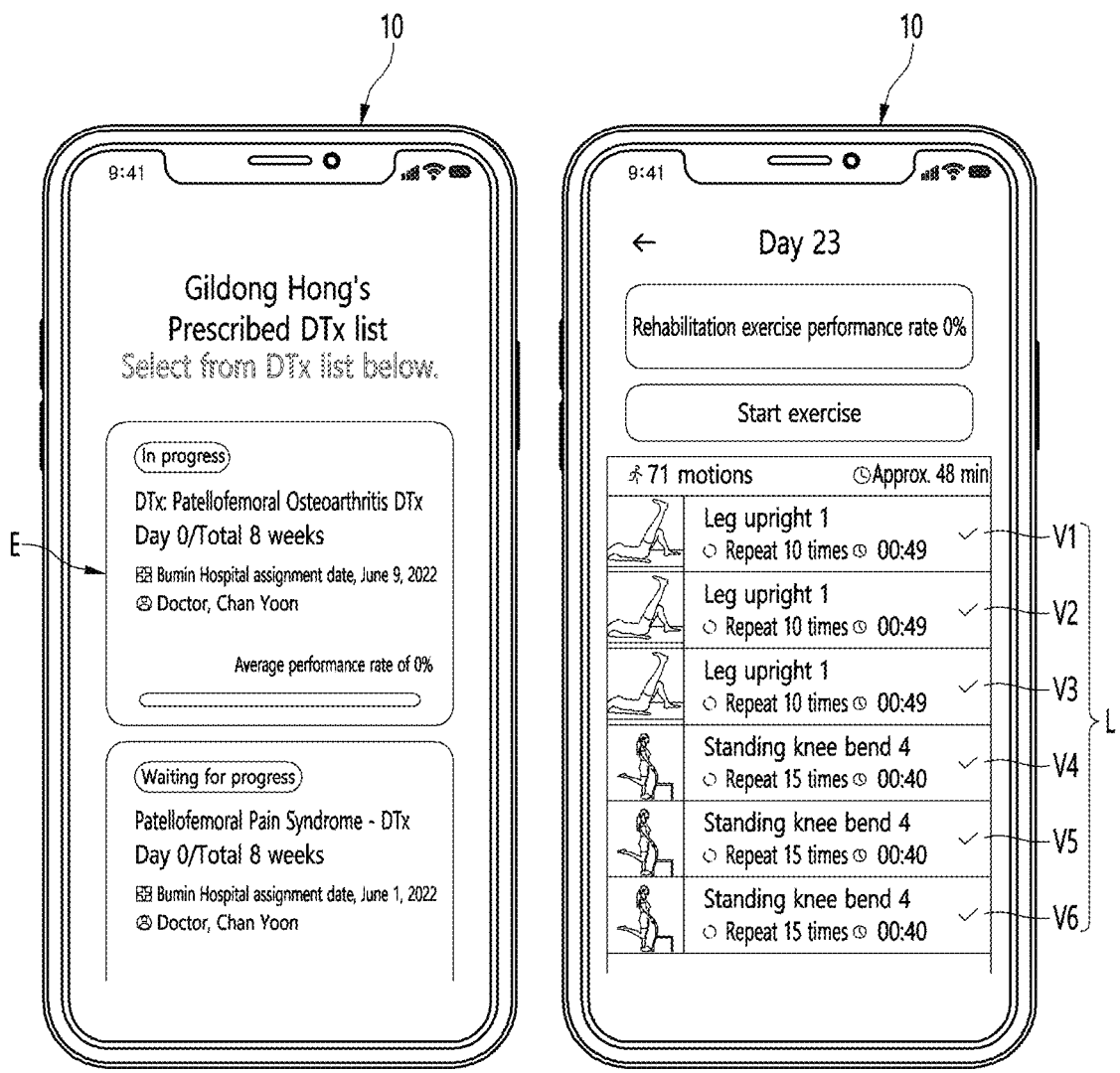
FIGS. 5 and 6 are conceptual views for describing a method of analyzing an exercise motion of a patient from an exercise image.

Hereinafter, with reference to the accompanying drawings, a method and system for providing exercise therapy using an artificial intelligence posture estimation model and a motion analysis model according to the present invention will be described in detail. FIG. 1 is a conceptual view for describing a system for providing exercise therapy according to the present invention. FIGS. 2 and 3 are flowcharts for describing a method of providing exercise therapy according to the present invention, FIGS. 4A and 4B are conceptual views for describing a doctor's prescription, FIGS. 5 and 6 are conceptual views for describing a method of analyzing an exercise motion of a patient from an exercise image, FIGS. 7, 8A, 8B, 8C, 8D, 8E, and 8F are conceptual views for describing an artificial intelligence posture estimation model, and FIGS. 9A, 9B, and 9C are conceptual views for describing a user environment in which an exercise motion analysis result of a patient is provided.

As illustrated in FIG. 1, a system 1000 for providing exercise therapy according to the present invention is capable of analyzing an exercise motion of a patient in an exercise image received from a patient terminal 10 using an artificial intelligence posture estimation and motion analysis model, and may be configured to include at least one of an application 100 installed on the patient terminal 10 or an artificial intelligence server (or cloud server) 200. Further, the system 1000 for providing exercise therapy according to the present invention may include a posture estimation model and a motion analysis model trained using training data.

The application 100 in the present invention may be installed on the patient terminal 10 to analyze an exercise motion of a patient U suffering from a musculoskeletal disease, and perform a function of providing feedback information based on an analysis result. Accordingly, the application 100 according to the present invention may be referred to as a "digital exercise therapy solution", "digital rehabilitation therapy solution", "digital exercise evaluation solution", "contactless exercise therapy solution", "contactless rehabilitation therapy solution", "contactless exercise evaluation solution", "mobile exercise therapy program", "mobile rehabilitation therapy program", "mobile exercise evaluation program", and "mobile orthopedic rehabilitation assistant (MORA)".

The application 100 according to the present invention may be installed on the patient terminal 10 to connect the patient U of a musculoskeletal disease with an orthopedic doctor D to perform a role in assisting the patient U in rehabilitation. Hereinafter, for convenience of description, the application 100 installed on the patient terminal 10 will be described to be referred to as an "exercise therapy application".

Meanwhile, the exercise therapy application 100 according to the present invention may be installed on the patient terminal 10. The patient terminal 10 described in the present invention means an electronic device logged in with a user account of the patient U. For example, the electronic device may include at least one of a smart phone, a cell phone, a tablet PC, a kiosk, a computer, a laptop, a digital broadcasting terminal, a personal digital assistant (PDA), or a portable multimedia player (PMP).

Here, the user account of the patient U may mean an account of the patient U registered in the system 1000 for providing exercise therapy according to the present invention. The user account of the patient U may be understood as a "patient account" or "patient ID" (identification or identification number). In the present invention, the terms "patient", "patient account (or a user account of a patient)" and "patient terminal" may be used interchangeably.

Meanwhile, the doctor may provide a prescription related to an exercise to the patient U through a doctor terminal 20. In the present invention, the doctor terminal 20 may mean an electronic device logged in with a user account of the doctor D. The user account of the doctor D is an account of the doctor D registered in the system 1000 for providing exercise therapy according to the present invention, which may be understood as a "doctor account" or "doctor ID" (identification or identification number). In the present invention, the terms "doctor", "doctor account" (or a user account of a doctor), and "doctor terminal" may be used interchangeably.

The doctor D may provide a prescription for the patient U with reference to a user DB 30 that includes the user information of the patient U.

User information (or patient information) of the patient U matched to each patient account may exist in the user DB 30. The user information of the patient U may include various information needed to provide exercise therapy. For example, the user information of the patient U may include at least one of disease information, age information, gender information, surgical history information, exercise plan information, exercise performance information, height information, or weight information of the patient U. However, the user information of the patient described above is just illustrative, and it is obvious that the user information of the patient may include various information necessary to provide exercise therapy to the patient.

Meanwhile, the exercise therapy application 100 described in the present invention is installed on the patient terminal 10 and may analyze an exercise motion of the patient who performed the exercise according to the prescription of the doctor D, through the artificial intelligence posture estimation model and the artificial intelligence motion analysis model, and provide the analysis on the patient terminal 10.

Further, the exercise therapy application 100 may be configured to communicate with the artificial intelligence server 200, and may provide the exercise motion analysis result of the patient analyzed by the artificial intelligence server 200 to the patient terminal 10. The exercise motion analysis result of the patient analyzed by the artificial intelligence server 200 may be generated by at least one of an artificial intelligence motion analysis unit 212 and a rule-based motion analysis unit 213 included in a motion analysis unit 210.

The exercise therapy application 100 is configured to transmit and receive mutual data through wireless communication with the artificial intelligence server 200, and a wireless communication method is not limited. The exercise therapy application 100 according to the present invention may perform communication with the artificial intelligence server 200 using a communication module provided on the patient terminal 10. The communication module provided in the patient terminal 10 may vary.

For example, the communication module provided in the patient terminal 10 may be configured to perform the communication with the artificial intelligence server 200 using at least one of wireless LAN (WLAN), wireless-fidelity (Wi-Fi), wireless-fidelity (Wi-Fi) direct, digital living network alliance (DLNA), wireless broadband (WiBro), world interoperability for microwave access (WiMAX), high speed downlink packet access (HSDPA), high speed uplink packet access (HSUPA), long term evolution (LTE), long term evolution-advanced (LTE-A), fifth generation mobile telecommunication (5G), Bluetooth™ radio frequency identification (RFID), infrared communication (infrared data association (IrDA)), ultra-wideband (UWB), ZigBee, near field communication (NFC), Wi-Fi direct, or wireless universal serial bus (wireless USB) technologies.

Meanwhile, the artificial intelligence server 200 described in the present invention may be a cloud server that performs an exercise motion analysis of the patient U from an exercise image. The artificial intelligence server 200 may perform an analysis of the exercise motion of the patient U using the exercise image received from the exercise therapy application 100. The "artificial intelligence server" described in the present invention may be referred to as an "artificial intelligence exercise therapy server", "artificial intelligence rehabilitation therapy server", "digital therapy server", etc. Hereafter, for convenience of description, this will be described to be referred to as an "artificial intelligence server".

Figure 7:
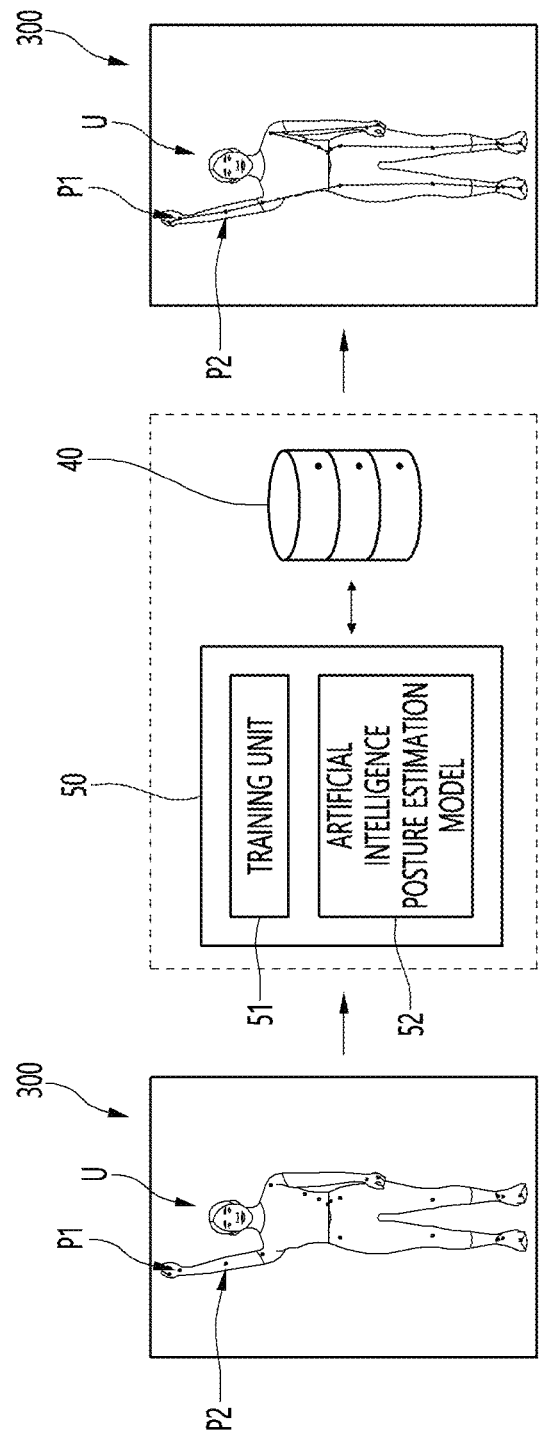

Meanwhile, at least one of the exercise therapy application 100 or the artificial intelligence server 200 according to the present invention may analyze a relative positional relationship between keypoints P1 and P2 corresponding to a plurality of joint points of the patient U extracted from an exercise image 300 through a posture estimation model 52 (corresponding to the artificial intelligence posture estimation unit 121*a* in FIG. 1) trained using training data related to the joint points, as illustrated in FIG. 7. The analysis of the relative positions of the keypoints may be performed by the motion analysis unit 120 or 210. In particular, the exercise motion analysis may be performed by one of the artificial intelligence motion analysis unit 122 or 212 and the rule-based motion analysis unit 123 or 213 of the motion analysis unit. One of the artificial intelligence motion analysis unit 122 or 212 or the rule-based motion analysis unit 123 or 213 may be referred to as an artificial intelligence motion analysis model.

Here, the term "joint point" may mean a plurality of joints of the patient U (or a part of the body of the patient U that includes joints).

Further, the term "keypoint" may mean an area corresponding to each of a plurality of joint points of the subject U in the exercise image 300.

Accordingly, in the present invention, the terms "joint point" and "keypoint" may be used interchangeably, and each of the joint point and keypoint may be described by assigning the same reference numeral "P2".

The system 1000 for providing exercise therapy may, using the posture estimation model 52, extract the keypoints P1 and P2 corresponding to the joint points from the exercise image of the patient, and analyze the exercise motion of the patient U based on the analysis of the positional relationship between the extracted keypoints P1 and P2. In the present invention, a series of processes for analyzing an exercise motion of a patient from an exercise image using keypoints extracted through the artificial intelligence posture estimation model 52 may be referred to as an "exercise motion analysis process".

The exercise motion analysis process may be performed by at least one of the exercise therapy application 100 or the artificial intelligence server 200. Specifically, the exercise motion analysis process may include at least one of: i) a first data processing method performed by the exercise therapy application 100, ii) a second data processing method performed by the artificial intelligence server 200, or iii) a third data processing method performed by both the exercise therapy application 100 and the artificial intelligence server 200.

Here, the third data processing method may be performed sequentially or simultaneously in each of the exercise therapy application 100 and the artificial intelligence server 200.

Accordingly, in the present invention, the exercise motion analysis process may be described to be performed in the system 1000 for providing exercise therapy, without distinguishing a physical space and a subject in which the exercise motion analysis process is performed.

Meanwhile, as illustrated in FIG. 7, the exercise motion analysis process may be performed using the keypoints extracted from the artificial intelligence posture estimation model 52. The artificial intelligence posture estimation model 52 may specify or estimate a joint point of a patient from an exercise image through learning on training data specialized for the joint point, and extract a corresponding keypoint.

In the present invention, the training data on which the artificial intelligence posture estimation model 52 is trained may be stored in a database 40, which may also be referred to as a "training data DB". More details on the training data will be described below.

As illustrated in FIG. 7, the posture estimation server 50 may include at least one of a training unit 51 or a posture estimation model 52. The posture estimation server 50 may be provided inside the system 1000 for providing exercise therapy according to the present invention, or may be configured as an external server. That is, the posture estimation server 50 according to the present invention may be understood as performing a function of performing learning for posture estimation, and not being constrained by a physical space. The details of the posture estimation server 50 are described below along with the training data.

Meanwhile, as illustrated in FIG. 1, the exercise therapy application 100 according to the present invention may include a configuration of at least one of an image receiving unit 110, the motion analysis unit 120, an image processing unit 130, or a control unit 140.

The image receiving unit 110 of the exercise therapy application 100 may be configured to receive an exercise image including an image of a patient exercising from the patient terminal 10 on which the application 100 is installed. Such an exercise image may be photographed by a camera installed on the patient terminal 10. In the present invention, "receiving an exercise image from the patient terminal 10" may be understood to mean that the image receiving unit 110 of the exercise therapy application 100 accesses an exercise image recorded in a memory of the patient terminal 10.

The motion analysis unit 120 of the exercise therapy application 100 may perform an analysis of the exercise motion (or exercise posture) of the patient based on an exercise image received from the patient terminal 10. To this end, the motion analysis unit 120 of the exercise therapy application 100 may be configured to include a configuration of at least one of a keypoint extraction unit 121, the artificial intelligence motion analysis unit 122, or the rule-based motion analysis unit 123. The artificial intelligence motion analysis unit 122 or the rule-based motion analysis unit 123 may be referred to as an "artificial intelligence motion analysis model".

The keypoint extraction unit 121 may, from the exercise image, extract the keypoints P1 and P2 that is configured in the form of paired x-axis and y-axis coordinate information. In this case, the keypoint extraction unit 121 may extract the keypoints from an image using the artificial intelligence model.

In the present invention, the keypoint extraction using the artificial intelligence model may be described as being performed by the artificial intelligence posture estimation unit 121a included in the keypoint extraction unit 121.

The artificial intelligence posture estimation unit 121a may be referred to as an "artificial intelligence posture estimation model" and may extract a keypoint corresponding to a joint point of a patient from an exercise image using the artificial intelligence model trained for object detection from an image. The artificial intelligence posture estimation model may be a model based on the object detection. For example, the artificial intelligence posture estimation unit 121a may extract keypoints from an exercise image using an object detection artificial intelligence model that ensembles a plurality of bounding boxes. Meanwhile, the artificial intelligence posture estimation unit 121a may use various object detection artificial intelligence models, and the object detection artificial intelligence model described above corresponds to an example.

Further, in the present invention, the artificial intelligence motion analysis unit 122 and the rule-based motion analysis unit 123 may perform an analysis of an exercise motion (or exercise posture) of a patient using at least one of an exercise image received from the patient terminal or a keypoint extracted from the keypoint extraction unit 120.

More specifically, the artificial intelligence motion analysis unit 122 and the rule-based motion analysis unit 123 may: i) perform an analysis of an exercise motion of a patient based on an exercise image, ii) perform an analysis of an exercise motion of a patient based on a keypoint, or iii) perform an analysis of an exercise motion of a patient using both an exercise image and keypoint.

Hereinafter, for convenience of description, a method of analyzing an exercise motion of a patient based on a keypoint will be mainly described. However, it is obvious that the artificial intelligence motion analysis unit 122 and the rule-based motion analysis unit 123 receive an exercise image rather than a keypoint as input data and may perform an exercise motion analysis of a patient directly from the exercise image. Meanwhile, the artificial intelligence motion analysis unit 122 or the rule-based motion analysis unit 123 may also be expressed as the aforementioned "artificial intelligence motion analysis model".

Meanwhile, the artificial intelligence motion analysis unit 122 may, based on an artificial intelligence model (or the posture estimation model, see reference numeral "52" in FIG. 7) trained to analyze an exercise motion (or exercise posture) of a patient from a keypoint, perform an exercise type classification (or exercise type specification) of an exercise performed by the patient, and an accuracy judgment of the exercise motion.

Furthermore, the rule-based motion analysis unit 123 may, based on rule information defined for analyzing an exercise motion of a patient, perform the exercise type classification (or exercise type specification) of the exercise performed by the patient, and the accuracy judgment of the exercise motion.

Here, the "rule information" is information including various rules used to analyze the exercise motion, which may include, for example, standard joint range of motion information for each exercise motion (or exercise type). The term "rule information" may be used interchangeably with terms such as "reference information" and "standard information".

Further, the rule information may include, in addition to the range of motion of a joint, various rule information for performing an analysis of at least one of a distance of motion of a joint, a speed (or acceleration) of motion of a joint, a body balance of a subject (corresponding to a patient) included in an exercise image targeted for analysis, a body balance, or a body alignment state (e.g., an axial alignment state of a leg, a spinal alignment state, etc.). The rule-based motion analysis unit 123 may derive various analysis results from the exercise image of the patient targeted for analysis based on the rule information.

In the present invention, an analysis of an exercise motion of a patient from an exercise image may be performed by at least one of the artificial intelligence motion analysis unit 122 or the rule-based motion analysis unit 123.

Specifically, in the present invention, i) an analysis of an exercise motion of a patient may be performed by the artificial intelligence motion analysis unit 122 (a "first analysis performance method"), ii) an analysis of an exercise motion of a patient may be performed by the rule-based motion analysis unit 123 (a "second analysis performance method"), or iii) an analysis of an exercise motion of a patient may be performed by both the artificial intelligence motion analysis unit 122 and the rule-based motion analysis unit 123 (a "third analysis performance method").

Here, in the third analysis performance method, data processing may be performed sequentially or simultaneously in each of the artificial intelligence motion analysis unit 122 and the rule-based motion analysis unit 123.

Meanwhile, the image processing unit 130 of the exercise therapy application 100 may be configured to overlap or render graphic objects corresponding to the extracted keypoints P1 and P2 on the subject U of the patient included in the exercise image 300. This allows the patient to intuitively recognize the joint points that are being analyzed for the exercise motion of the patient.

The control unit 140 of the exercise therapy application 100 may be configured to perform an overall control of the configurations included in the exercise therapy application 100. The control unit 140 of the exercise therapy application 100 may control the configurations of the exercise therapy application 100 using a central processing unit (CPU) of the patient terminal 10, and may further perform a control of the configurations (e.g., a communication module, a camera module, a sensing module, an output module (e.g., a display, a speaker), and an input module (e.g., a touch screen, a microphone) provided in the patient terminal 10.

Meanwhile, as illustrated in FIG. 1, the artificial intelligence server 200 is a cloud server configured to perform exercise posture of a patient using the artificial intelligence posture estimation model, and may be configured to include a configuration of at least one of a motion analysis unit 210 or a control unit 220.

The motion analysis unit 210 of the artificial intelligence server 200 may perform an analysis of the exercise motion (or exercise posture) of the patient based on an exercise image received from the patient terminal 10.

The motion analysis unit 210 of the artificial intelligence server 200 may receive an exercise image of a patient from the exercise therapy application 100, and the receiving of the exercise image may be performed by a communication unit (or communication module) of the artificial intelligence server 200.

The motion analysis unit 210 of the artificial intelligence server 200 may be configured to include a configuration of at least one of a keypoint extraction unit 211, an artificial intelligence motion analysis unit 212, or a rule-based motion analysis unit 213. The artificial intelligence motion analysis unit 212 or the rule-based motion analysis unit 213 may be referred to as an "artificial intelligence motion analysis model".

Each of the keypoint extraction unit 211, artificial intelligence motion analysis unit 212, and rule-based motion analysis unit 213 included in the artificial intelligence server 200 may perform the same functions as the keypoint extraction unit 121, artificial intelligence motion analysis unit 122, and rule-based motion analysis unit 123 of the previously described exercise therapy application 100. In this regard, a detailed description will be omitted.

The control unit 220 of the artificial intelligence server 200 may be configured to perform an overall control of the configurations included in the artificial intelligence server 200.

Hereinafter, an exercise motion analysis process for analyzing an exercise motion of the patient U from an exercise image and providing an exercise motion analysis result will be described using the configuration above of the system 1000 for providing exercise therapy according to the present invention.

As illustrated in FIG. 2, an exercise prescription for the patient U may be made in the doctor terminal 20 (S210), and the system 1000 for providing exercise therapy may, based on the exercise prescription made for the patient in the doctor terminal 20, receive prescription information on the exercise prescription from the doctor terminal 20.

The system 1000 for providing exercise therapy may, based on the prescription information being received from the doctor terminal 20, allocate, to a patient account, an exercise plan that includes at least one prescribed exercise according to the prescription information. The allocated exercise plan may be transmitted to the patient terminal 10 (S220).

The system 1000 for providing exercise therapy may include a communication unit that performs communication with at least one of the patient terminal 10, the doctor terminal 20, the user DB 30, or the database 40. For example, the communication unit may perform the communication using at least one of wireless LAN (WLAN), wireless-fidelity (Wi-Fi), wireless-fidelity (Wi-Fi) direct, digital living network alliance (DLNA), wireless broadband (WiBro), world interoperability for microwave access (WiMAX), high speed downlink packet access (HSDPA), high speed uplink packet access (HSUPA), long term evolution (LTE), long term evolution-advanced (LTE-A), fifth generation mobile telecommunication (5G), Bluetooth™ radio frequency identification (RFID), infrared communication (infrared data association (IrDA)), ultra-wideband (UWB), ZigBee, near field communication (NFC), Wi-Fi direct, or wireless universal serial bus (wireless USB) technologies.

Meanwhile, an exercise image of the patient performing the prescribed exercise included in the exercise plan may be photographed in the patient terminal 10 (S230). The exercise therapy application 100 may activate a camera provided on the patient terminal 10 to control the exercise image to be photographed.

The exercise image photographed at the patient terminal 10 may be used as analysis target data (or exercise image targeted for analysis) for an exercise motion analysis of the patient by the system 1000 for providing exercise therapy.

As described above, the exercise motion analysis process may be performed in at least a portion of the exercise therapy application 100 installed on the patient terminal 10 or the artificial intelligence server 200, and may be described in the present invention as being performed in the system 1000 for providing exercise therapy, without separately distinguishing a physical space where the exercise motion analysis process is performed and a subject.

Meanwhile, the system 1000 for providing exercise therapy may extract the keypoints P1 and P2 corresponding to a plurality of joint points from the exercise image. The extracting of the keypoints P1 and P2 may be performed by at least a portion of the keypoint extraction unit 121 included in the exercise therapy application 100 or the keypoint extraction unit 121 included in the artificial intelligence server 200.

The system 1000 for providing exercise therapy may perform an analysis of a relative positional relationship between the extracted keypoints P1 and P2 (S250). Further, the system 1000 for providing exercise therapy may analyze the exercise motion of the patient U based on the analysis of the positional relationship between the keypoints P1 and P2 (S260). This exercise motion analysis may be performed by at least a portion of the motion analysis unit 120 of the application 100 or the motion analysis unit 210 of the artificial intelligence server 200.

Further, the system 1000 for providing exercise therapy may provide an exercise motion analysis result of the patient U as feedback information to the patient terminal 10 and as monitoring information to the doctor terminal 20 (S270).

As described above, the system 1000 for providing exercise therapy may perform an overall control of the exercise motion analysis process, which, in the present invention, may be understood to be performed by the control unit of the system 1000 for providing exercise therapy. That is, the control unit of the system 1000 for providing exercise therapy is a concept that includes the control unit 140 of the exercise therapy application 100 and the control unit 220 of the artificial intelligence server 200, which may perform an overall control of the system 1000 for providing exercise therapy.

Hereinafter, the exercise motion analysis process performed by system 1000 for providing exercise therapy will be described in more detail.

In the present invention, a process of receiving, from the doctor terminal, prescription information related to an exercise for a patient may proceed (S310, see FIG. 3).

As illustrated in FIGS. 4A and 4B, system 1000 for providing exercise therapy may provide an exercise prescription page (or exercise assignment page) that includes a prescription function related to an exercise for a patient, on the doctor terminal 20 logged in with a doctor account. In the present invention, the term "exercise prescription" may be used interchangeably with the term "exercise assignment".

The system 1000 for providing exercise therapy may provide, on the doctor terminal 20, an exercise prescription page for each patient account, such that a prescription may be made for a specific patient U account among the patient accounts matched to the doctor account.

For example, in the present invention, assume that a specific doctor D account is matched with a first patient account (e.g., patient account "Wooyoung Kim") and a second patient account (e.g., patient account "Sohee Kim"). The system 1000 for providing exercise therapy may provide, on the doctor terminal 20, an exercise prescription page corresponding to the first patient account (e.g., patient account "Wooyoung Kim") based on an exercise prescription request for the first patient account being received from the doctor terminal 20.

The system 1000 for providing exercise therapy may receive, based on a user selection (or user input) made on the exercise prescription page corresponding to the specific patient, prescription information for the specific patient from the doctor terminal 20. The prescription information may include a variety of information for prescribing an exercise to a patient. For example, the prescription information may include at least one of: i) information on at least one exercise motion that should be included in an exercise plan (e.g., "Calf stretch against a wall", "Seated rolling ball sole massage"), ii) difficulty information on the exercise motion, iii) duration information on the exercise motion, iv) information on the number of times to perform the exercise motion, v) schedule information on performing the exercise motion, vi) body information matched to the exercise motion (e.g., "Ankle" and "Knee"), or vii) caution information (e.g., "After the exercise, please apply an ice pack") (see FIG. 4A and (a) of FIG. 4B).

The system 1000 for providing exercise therapy may receive prescription information for the specific patient U from the doctor terminal 20 based on the prescription information on the specific patient being input (or selected) on the exercise prescription page corresponding to the specific patient. In this case, guidance information may be output on the doctor terminal 20 to guide that a prescription has been made for the specific patient (see (b) of FIG. 4B).

Meanwhile, in the present invention, based on the prescription information, a process of allocating an exercise plan including at least one prescribed exercise to a patient account may proceed (S320, see FIG. 3).

As illustrated in FIG. 5, the system 1000 for providing exercise therapy may, based on the prescription information on the specific patient U, allocate an exercise plan E including at least one prescribed exercise to the specific patient account, and provide the allocated exercise plan (e.g., "Patellofemoral osteoarthritis digital therapy", E) to the patient terminal 10 logged in with the specific patient account.

Herein, the term "prescribed exercise" may be understood as an exercise motion that is specified and allocated to a patient account based on prescription information among a plurality of exercise motions (or exercise types) included in the system 1000 for providing exercise therapy. Accordingly, in the present invention, the term "prescribed exercise" may be used interchangeably with the term "exercise motion". Further, in the present invention, the term "exercise plan" may be used interchangeably with the term "digital therapy".

The system 1000 for providing exercise therapy may, based on receiving a request to provide an exercise plan allocated to a specific patient account from a patient terminal 10 logged in with the specific patient account, provide an exercise page, on the patient terminal 10, associated with an exercise guide image providing function, for the patient to perform a prescribed exercise included in the exercise plan.

As illustrated in FIG. 5, the exercise page may include an exercise list L, in which the exercise list L may include items V1 to V6 corresponding to exercise guide images for each of a plurality of prescribed exercises (e.g., "Leg upright" and "Standing knee bend") included in the exercise plan allocated to the specific account.

The system 1000 for providing exercise therapy may, when the exercise plan includes a specific prescribed exercise (e.g., "Leg upright") having a plurality of exercise sets, control such that the items V1 to V3 corresponding to the exercise guide image of the specific prescribed exercise are included in an exercise list L by the number of the sets (e.g., " ").

Meanwhile, the system 1000 for providing exercise therapy may, based on receiving a request to start an exercise from the patient terminal 10, control such that a plurality of exercise guide images are played sequentially on the patient terminal 10 based on a sequence of items V1 to V6 included in the exercise list L.

Meanwhile, in the present invention, a process of receiving, from the patient terminal, an exercise image that photographs an exercise according to the prescribed exercise may be performed (S330, see FIG. 3).

As illustrated in FIG. 6, the system 1000 for providing exercise therapy may control a camera provided on the patient terminal 10 to photograph an exercise image of the patient U based on the exercise guide image being played on the patient terminal 10.

The exercise therapy application 100 installed on the patient terminal 10 may control an activation state of a camera provided on the patient terminal 10 from an inactive state to an active state, such that the camera is controlled to photograph an exercise image of the patient U performing an exercise motion according to the exercise guide image.

As illustrated in FIG. 6A, the exercise therapy application 100 may, in order to detect a subject U corresponding to the patient from the exercise image being photographed through the camera, output a guidance message (e.g., "Please stand inside the screen") on the patient terminal 10 such that the entire body of the patient is included within a specific area of the exercise image (or a display of the patient terminal).

The exercise therapy application 100 may, based on the subject U corresponding to the entire body of the patient being included within the specific area, detect the subject U from an image 300 using an object detection algorithm.

The exercise therapy application 100 may use a variety of object detection algorithms. For example, the exercise therapy application 100 may use an algorithm (weighted box fusion (WBF)) that ensembles a plurality of bounding boxes. However, it is obvious that the exercise therapy application 100 is not limited to the object detection algorithm described above, but may utilize various object detection algorithms that are capable of detecting an object corresponding to the subject U from the training target exercise image 300.

Further, the exercise therapy application 100 may, based on the subject U corresponding to the entire body of the patient being detected within the specific area, photograph, through the camera, an exercise image of the patient performing an exercise motion according to the prescribed exercise.

In this case, the exercise therapy application 100 may photograph the patient performing the prescribed exercise in a state where an exercise guide image corresponding to the prescribed exercise allocated to the patient is played.

Further, the exercise therapy application 100 may control an exercise image that is photographed by the camera of the patient terminal 10 to be matched to an exercise plan (or each of a plurality of prescribed exercises included in the exercise plan) and recorded in the memory of the patient terminal 10.

Meanwhile, in the present invention, a process of extracting a keypoint corresponding to each of a plurality of preset joint points from the exercise image may proceed (S340, see FIG. 3).

In the present invention, keypoints P1 and P2 corresponding to joint points P1 and P2 preset from the exercise image may be extracted by at least a portion of the exercise therapy application 100 or the artificial intelligence server 200. As described above, the extraction of the keypoints P1 and P2 may be performed by: i) the exercise therapy application 100, ii) the artificial intelligence server 200, or iii) both the exercise therapy application 100 and the artificial intelligence server 200. Hereinafter, it will be described that the extraction of keypoints P1 and P2 is performed by the system 1000 for providing exercise therapy, without separately distinguishing the subject that performs the extraction.

The system 1000 for providing exercise therapy may extract, from the exercise image 300, areas corresponding to predefined (or preset) joint points of the plurality of joint points of the patient as keypoints P1 and P2.

Here, the term "joint point" may mean a plurality of joints of the patient U (or a part of the body of the patient U that includes joints).

Further, the term "keypoint" may mean an area corresponding to each of a plurality of joint points of the subject U in the exercise image 300.

In the present invention, the terms "joint point" and "keypoint" may be used interchangeably, and each of the joint point and keypoint may be described by assigning the same reference numeral "P1 or P2".

Meanwhile, the human body is made up of more than 200 bones, and a joint is a part where bone connects to each other, and the human body may consist of a plurality of joints.

In the present invention, among the plurality of joint points constituting the human body, joint points that are targeted as keypoints are predesignated and may exist as joint point definition information 500. For example, in the joint point definition information 500, a first joint point P1 corresponding to a center of the head 510 and a second joint point P2 corresponding to a center of the neck 520 may exist to be predefined (see FIG. 8D).

The system 1000 for providing exercise therapy may, based on the posture estimation model 52 trained using a training data set including position information on preset joint points, extract the keypoints P1 and P2 corresponding to the joint points from the exercise image 300.

In this case, the system 1000 for providing exercise therapy may, based on the position information of each of the joint points preset by the posture estimation model being extracted in the form of paired x-axis and y-axis coordinate information, specify the positions of the keypoints P1 and P2 in the exercise image 300.

Meanwhile, the system 1000 for providing exercise therapy may, based on whether the joint point is visible in the exercise image 300, extract (or specify) the keypoints P1 and P2 corresponding to the joint points according to any one process of a first keypoint extraction process or a second keypoint extraction process.

In the present invention, whether a joint point is visible may be understood to mean whether the joint point is visible in the exercise image 300.

The system 1000 for providing exercise therapy may judge that the joint point of the exercise image 300 is visible when the exercise image 300 includes a body part of the subject U that corresponds to the joint point.

The system 1000 for providing exercise therapy may, when a specific joint point is visible in the exercise image 300, extract a keypoint corresponding to the specific joint point according to the first keypoint extraction process.

Specifically, the system 1000 for providing exercise therapy may specify a visible joint point of the subject U that is visible in the exercise image 300 among a plurality of preset joint points. For example, the system 1000 for providing exercise therapy may, when a first joint point and a second joint point of the plurality of preset joint points are visible in the exercise image, specify the first joint point and the second joint point as visible joint points.

Further, the system 1000 for providing exercise therapy may extract the specified visible joint point as a keypoint.

In this case, the system 1000 for providing exercise therapy may extract position information on an area (or pixel) corresponding to the visible joint point in the exercise image to extract a keypoint corresponding to the visible joint point. For example, the system 1000 for providing exercise therapy may extract position information on a visible joint point using the object detection algorithm to extract a keypoint corresponding to the visible joint point.

In the present invention, the position information of the visible joint point extracted according to the first keypoint extraction process may be described to be referred to as a "first type of information (first type of position information)" or "substantial position information".

In contrast, the system 1000 for providing exercise therapy may judge that the joint point of the exercise image 300 is invisible when the exercise image 300 does not include a body part of the subject U that corresponds to the joint point.

The system 1000 for providing exercise therapy may, when a specific joint point is invisible in the exercise image 300, predict and extract a keypoint corresponding to the specific joint point using the posture estimation model 52 according to the second keypoint extraction process.

The system 1000 for providing exercise therapy may, based on the posture estimation model 52, predict position information of an invisible joint point of the subject U that is not visible in the exercise image 300 among the plurality of preset joint points. In this case, the posture estimation model 52 may predict the position information of the invisible joint point based on the position information of the visible joint point.

In the present invention, the position information of the joint point extracted according to the second keypoint extraction process may be described to be referred to as a "second type of information (second type of position information)" or "expected position information".

The system 1000 for providing exercise therapy may extract (or specify) the keypoint corresponding to the invisible joint point by matching the predicted position information on the invisible joint point to the keypoint corresponding to the invisible joint point.

As described above, in the present invention, the keypoints P1 and P2 corresponding to the joint points may be extracted (or specified) in the exercise image 300 according to different processes, based on the posture estimation model that has been performed training on the position information of the joint points, depending on whether the predefined joint points are visible. Therefore, in the present invention, it is also possible to analyze invisible joint points that are not visible in the exercise image.

Meanwhile, the system 1000 for providing exercise therapy may extract the keypoints P1 and P2 from the exercise image in real time in conjunction with the exercise image being photographed on the patient terminal 10. Further, the system 1000 for providing exercise therapy may provide the extracted keypoints P1 and P2 on the patient terminal 10 in real time such that the patient may intuitively recognize the joint points being analyzed for the exercise motion.

Specifically, as illustrated in FIGS. 6B and 6C, the system 1000 for providing exercise therapy may output the exercise image 300 in real time on the patient terminal 10 in conjunction with the exercise image 300 being photographed on the patient terminal 10. Further, the system 1000 for providing exercise therapy may provide a graphic object corresponding to the extracted keypoint P1 or P2 that overlaps an area of the subject U corresponding to the preset joint point.

Data processing to provide the keypoint graphic object overlapping the exercise image 300 may be performed by the image processing unit 130 of the exercise therapy application 100. The image processing unit 130 may render each of the graphic objects corresponding to the extracted keypoints P1 and P2 on the area of the subject U corresponding to the joint points P1 and P2 matched to the keypoints P1 and P2.

Further, the image processing unit 130 may, when a position of the preset joint point changes as the patient performs an exercise motion, provide a keypoint graphic object overlapping an area of the subject U corresponding to the changed joint point. That is, the image processing unit 130 may allow the keypoint graphic object to overlap the area corresponding to the joint point in the exercise image such that the position of the joint point that changes in real time is reflected.

Meanwhile, in the present invention, a process of analyzing a relative positional relationship between keypoints, from the keypoints extracted through the posture estimation model trained using training data related to the joint points, and analyzing an exercise motion of the patient for the prescribed exercise based on the analysis of the relative positional relationship may proceed (S350, see FIG. 3). The analysis of the relative positions of the keypoints may be performed by the motion analysis unit 120 or 210. In particular, the exercise motion analysis may be performed by one of the artificial intelligence motion analysis units 122 and 212 and the rule-based motion analysis units 123 and 213 of the motion analysis unit.

As illustrated in FIG. 6D, the exercise therapy application 100 may provide, on the patient terminal 10, guidance information to guide an analysis progression (e.g., "Calculating the result" or "Mr. Cheolsoo Kim, I will provide you with the exercise motion analysis result") to guide the patient through an exercise motion analysis. Hereinafter, a method of analyzing patient exercise motion will be described in detail.

The system 1000 for providing exercise therapy may analyze the relative positional relationship between the keypoints P1 and P2 corresponding to each of the plurality of preset joint points using the keypoints extracted from the posture estimation model trained using the training data.

The system 1000 for providing exercise therapy may analyze a relative position between the keypoints P1 and P2 corresponding to each of the plurality of preset joint points, using both the keypoints corresponding to visible joint points and the keypoints corresponding to invisible joint points.

Here, the "relative position between keypoints" may be understood as a position of one keypoint (e.g., a first keypoint, "P1") relative to another keypoint (e.g., a second keypoint, "P2"), between at least two keypoints P1 and P2.

Hereinafter, for convenience of description, a keypoint corresponding to a visible joint point will be referred to as a "first type keypoint" and a keypoint corresponding to an invisible joint point will be referred to as a "second type keypoint".

The system 1000 for providing exercise therapy may perform an analysis of at least one of: i) a relative positional relationship between a plurality of first type keypoints, ii) a relative positional relationship between a first type keypoint and a second type keypoint, or iii) a relative positional relationship between a plurality of second type keypoints.

In this case, the system 1000 for providing exercise therapy may, based on a type of prescribed exercise performed by the patient, analyze a relative positional relationship between some associated keypoints of the plurality of joint points.

For example, the system 1000 for providing exercise therapy may analyze a relative positional relationship between keypoints corresponding to each of a first joint point and a second joint point of the plurality of joint points when the patient performs a prescribed exercise according to a first exercise type.

In another example, the system 1000 for providing exercise therapy may analyze a relative positional relationship between keypoints corresponding to each of the first joint point and a third joint point of the plurality of joint points when the patient performs a prescribed exercise according to a second exercise type that is different from the first exercise type. This relative positional relationship may consequently be used for motion analysis.

The results of the motion analysis performed in the system 1000 for providing exercise therapy according to the present invention may vary widely. For example, the system 1000 for providing exercise therapy may, from the extracted keypoints or images, perform an analysis of at least one of a range of motion of a joint, a distance of motion, a speed (or acceleration) of motion of a joint, a body balance of a subject (corresponding to a patient) included in an exercise image targeted for analysis, a body balance, and a body alignment state (e.g., an axial alignment state of a leg, a spinal alignment state, etc.). Meanwhile, the system 1000 for providing exercise therapy according to the present invention may analyze a relative positional relationship between keypoints based on rule information related to a prescribed exercise.

Here, the rule information may be understood as information for which rules are predefined to analyze a relative positional relationship between keypoints.

The system 1000 for providing exercise therapy may analyze an exercise motion of a patient by judging whether a relative positional relationship between keypoints satisfies the rule information. Hereinafter, a method of analyzing a range of motion of a joint based on the relative positional relationship of keypoints and the rule information will be described as an example. However, the content described below is only one embodiment of analyzing a motion of a patient based on the relative positional relationship of keypoints and the rule information, and in the present invention, various motions of a patient may be analyzed based on the relative positional relationship of keypoints and the rule information.

The range of motion of a joint analyzed in the system 1000 for providing exercise therapy according to the present invention will be described in more detail below. The system 1000 for providing exercise therapy may, based on the rule information on standard range of motion of a joint related to a prescribed exercise, perform an analysis of a range of motion of a patient's joint depending on a relative positional relationship between keypoints.

Further, the system 1000 for providing exercise therapy may, based on the rule information related to the prescribed exercise, analyze a relative positional relationship between the keypoints. Further, the system 1000 for providing exercise therapy may analyze the exercise motion of the patient by judging whether the relative positional relationship between the keypoints satisfies the rule information.

The system 1000 for providing exercise therapy may extract, from a plurality of consecutive frames related to a specific prescribed exercise, a relative positional relationship between associated keypoints matched to the specific prescribed exercise, and obtain (or calculate) a range of motion of the patient's joint for the specific prescribed exercise using the extracted relative positional relationship.

Specifically, assume that an exercise image is configured with a plurality of frames of a first type corresponding to a first prescribed exercise and a plurality of frames of a second type corresponding to a second prescribed exercise.

The system 1000 for providing exercise therapy may, when an exercise motion analysis of a patient for the first prescription exercise of the first prescription exercise and the second prescription exercise is performed, analyze the exercise motion of the patient using keypoints extracted from the plurality of frames having the first type.

In contrast, the system 1000 for providing exercise therapy may, when an exercise motion analysis of a patient for the second prescription exercise is performed, analyze the exercise motion of the patient using keypoints extracted from the plurality of frames having the second type.

That is, the system 1000 for providing exercise therapy may analyze a keypoint positional relationship for consecutive movements (or posture) to obtain (or calculate) a range of motion for an exercise of the patient for a specific prescribed exercise.

Hereinafter, for convenience of description, a plurality of consecutive frames (i.e., a plurality of frames having a first type) corresponding to a specific prescribed exercise (e.g., the first prescribed exercise) will be referred to as a "first analysis target frame" and a "second analysis target frame," depending on the temporal sequence in which the frames are formed.

Here, it may be understood that the first analysis target frame is a frame formed temporally before, and the second analysis target frame is a frame formed temporally after.

The system 1000 for providing exercise therapy may extract keypoints from each of the first analysis target frame and the second analysis target frame.

A first analysis target keypoint group corresponding to each of the plurality of joint points may be extracted from the first analysis target frame, and a second analysis target keypoint group corresponding to each of the plurality of joint points may be extracted from the second analysis target frame.

The system 1000 for providing exercise therapy may analyze a "first positional relationship" between keypoints included in the first analysis target keypoint group and perform a first motion analysis of the subject U included in the first analysis target frame. In addition, the system 1000 for providing exercise therapy may analyze a "second positional relationship" between keypoints included in the second analysis target keypoint group and perform a second motion analysis of the subject U included in the second analysis target frame.

The system 1000 for providing exercise therapy may, based on the first keypoint positional relationship and the second keypoint positional relationship, obtain (extract or calculate) a range of motion of a patient's joint for a specific prescribed exercise.

In this case, the system 1000 for providing exercise therapy may obtain the range of motion of the patient's joint in consideration of at least one of age information, gender information, height information, weight information, surgery history information, or musculoskeletal disease information of the patient, with reference to the user DB 30.

Meanwhile, the system 1000 for providing exercise therapy may judge whether the obtained range of motion for the exercise of the patient satisfies the standard range of motion of a joint corresponding to the rule information related to the specific prescribed exercise. In the present invention, the rule-based analysis of the range of motion for the exercise of the patient may be performed by the rule-based motion analysis unit 213 of the artificial intelligence server 200 (see FIG. 1), but the analysis is not limited to being performed by the rule-based motion analysis unit 213.

In the present invention, there may be rule information on the standard range of motion of a joint for each of a plurality of exercise types. This rule information may include information on different standard range of motion of a joint by age, gender, height, weight, and musculoskeletal disease.

The system 1000 for providing exercise therapy may compare a patient's range of motion of a joint for a specific prescribed exercise to the standard range of motion of a joint for the specific prescribed exercise included in the rule information, and judge whether the patient's range of motion of a joint satisfies the standard range of motion of a joint.

The system 1000 for providing exercise therapy may, based on a judgment result, provide an analysis result of the exercise motion of the patient to the patient terminal 10 as feedback for the prescribed exercise.

Meanwhile, in the present invention, a process of transmitting the analysis result of the exercise motion of the patient to the patient terminal may be performed (S360, see FIG. 3).

The system 1000 for providing exercise therapy may provide a motion analysis result in a variety of ways in order for the patient to intuitively recognize the analysis result of the exercise motion and increase the compliance of the patient with the exercise.

The system 1000 for providing exercise therapy may provide graphic objects corresponding to the keypoints P1 and P2 overlapping the exercise image in real time in a state where the exercise image 300 is being photographed on the patient terminal 10 (see FIG. 6).

In this case, the system 1000 for providing exercise therapy may position information on the range of motion of the patient's joint, around the keypoints P1 and P2 related to the range of motion of the joint.

Further, the system 1000 for providing exercise therapy may provide keypoint graphic objects (or graphic objects corresponding to positional relationship between keypoints) having different visual appearances overlapping the exercise image to enable a patient to recognize whether the range of motion of the patient's joint satisfies the standard range of motion of a joint.

Further, the visual appearances of the graphic objects overlapping the exercise image may be configured to be different depending on whether the relative positional relationship between the extracted keypoints satisfies the rule information.

For example, when the range of motion of the patient's joint satisfies the standard range of motion of a joint, a graphical object A having a first visual appearance may overlap the exercise image 300. In contrast, when the range of motion of the patient's joint does not satisfy the standard range of motion of a joint, a graphic object B having a second visual appearance different from the first visual appearance may overlap the exercise image 300.

Further, the system 1000 for providing exercise therapy may, based on keypoints extracted from each of a plurality of frames constituting the exercise image 300, provide an evaluation score of the patient for the prescribed exercise (e.g., "Mr. Wooyoung Kim's squatting posture is 70 points") as the motion analysis result.

Meanwhile, in the present invention, the exercise therapy application 100 installed on the patient terminal 10 and the artificial intelligence server 200 may perform an analysis of the exercise motion and generate an exercise motion analysis result, respectively.

For example, the exercise therapy application 100 may allow graphical objects corresponding to the keypoints P1 and P2 to overlap the exercise image in real time to generate a first result analysis.

In another example, the artificial intelligence server 200, which is configured as a cloud server, may generate, based on keypoints extracted from each of the plurality of frames constituting the exercise image, an evaluation score of the patient for the prescribed exercise as a second analysis result.

The system 1000 for providing exercise therapy may provide, on the patient terminal 10, an analysis result of an exercise motion of the patient, including the first analysis result generated by the exercise therapy application 100 and the second analysis result generated by the artificial intelligence server 200.

Meanwhile, the system 1000 for providing exercise therapy may transmit an exercise motion analysis result of the patient to the doctor terminal 20. Both the first analysis result and the second analysis result may be provided to the doctor terminal 20.

As such, in the present invention, various user environments related to the provision of an analysis result are provided such that a patient may intuitively recognize the analysis result for an exercise motion. Another embodiment related to the provision of an analysis result will be described below.

Meanwhile, as illustrated in FIG. 7, the present invention is directed to analyzing an exercise motion of the patient U included in the exercise image 300 based on the exercise image 300 received from the patient terminal 10, and providing an analysis result. In particular, the present invention relates to a method of processing and learning a training data set centered on important joint points to analyze an exercise motion of a patient based on artificial intelligence.

Hereinafter, training data on which the posture estimation model of the present invention is trained will be described in detail.

As illustrated in FIG. 7, the database 40 is a storage where the training data set is stored, which may be provided on the system 1000 for providing exercise therapy according to the present invention itself or may be configured as an external storage (or an external DB). It may be understood that the database 40 according to the present invention is sufficient to be the space in which the training data set is stored, and is not limited by a physical space.

The present invention may be configured to include at least one of the database 40, the posture estimation server 50, or the system 1000 for providing exercise therapy.

In the database 40, training data for training the posture estimation model 52 may be stored as a training data set.

Figure 8B:
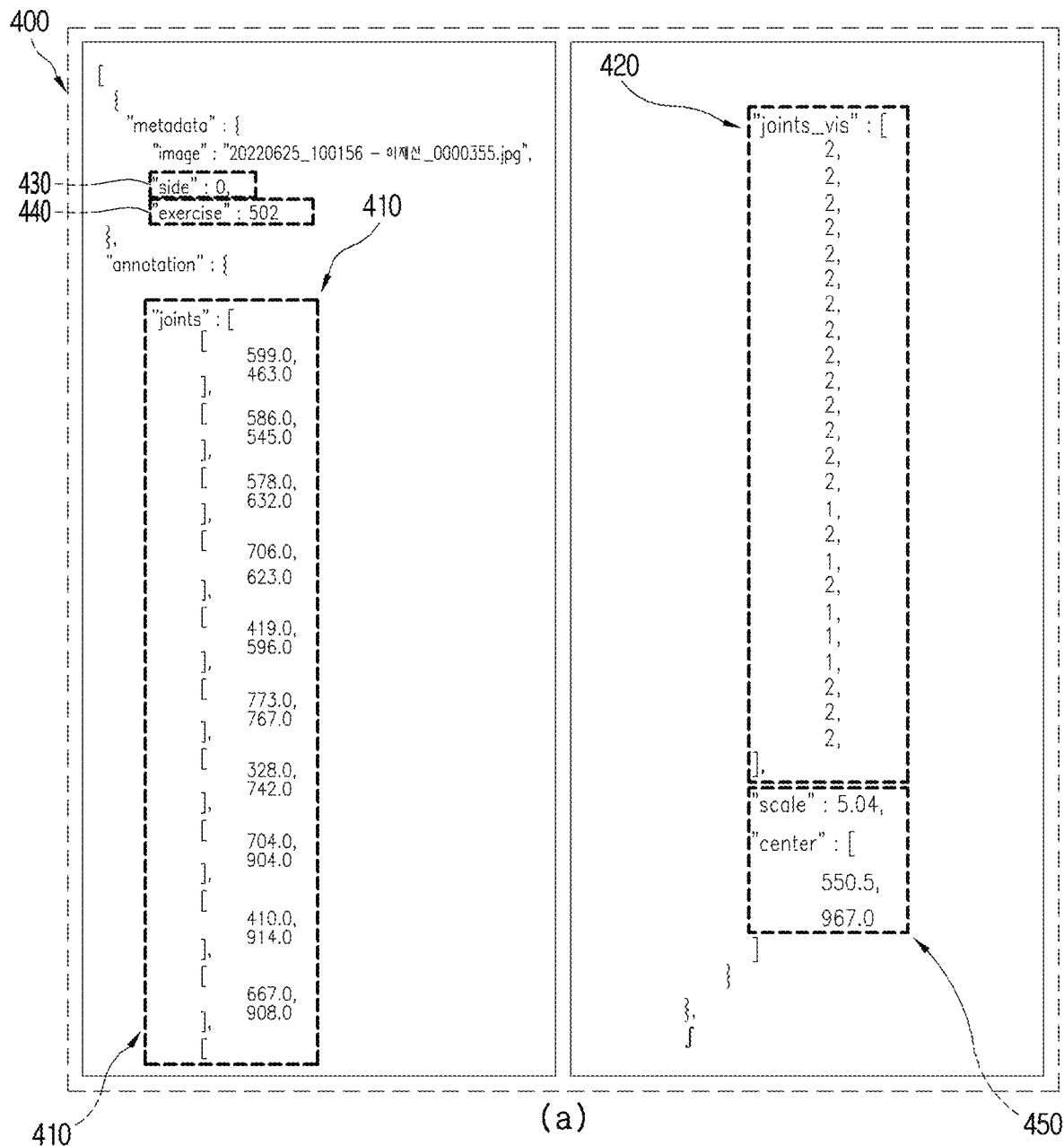
Figure 9A:
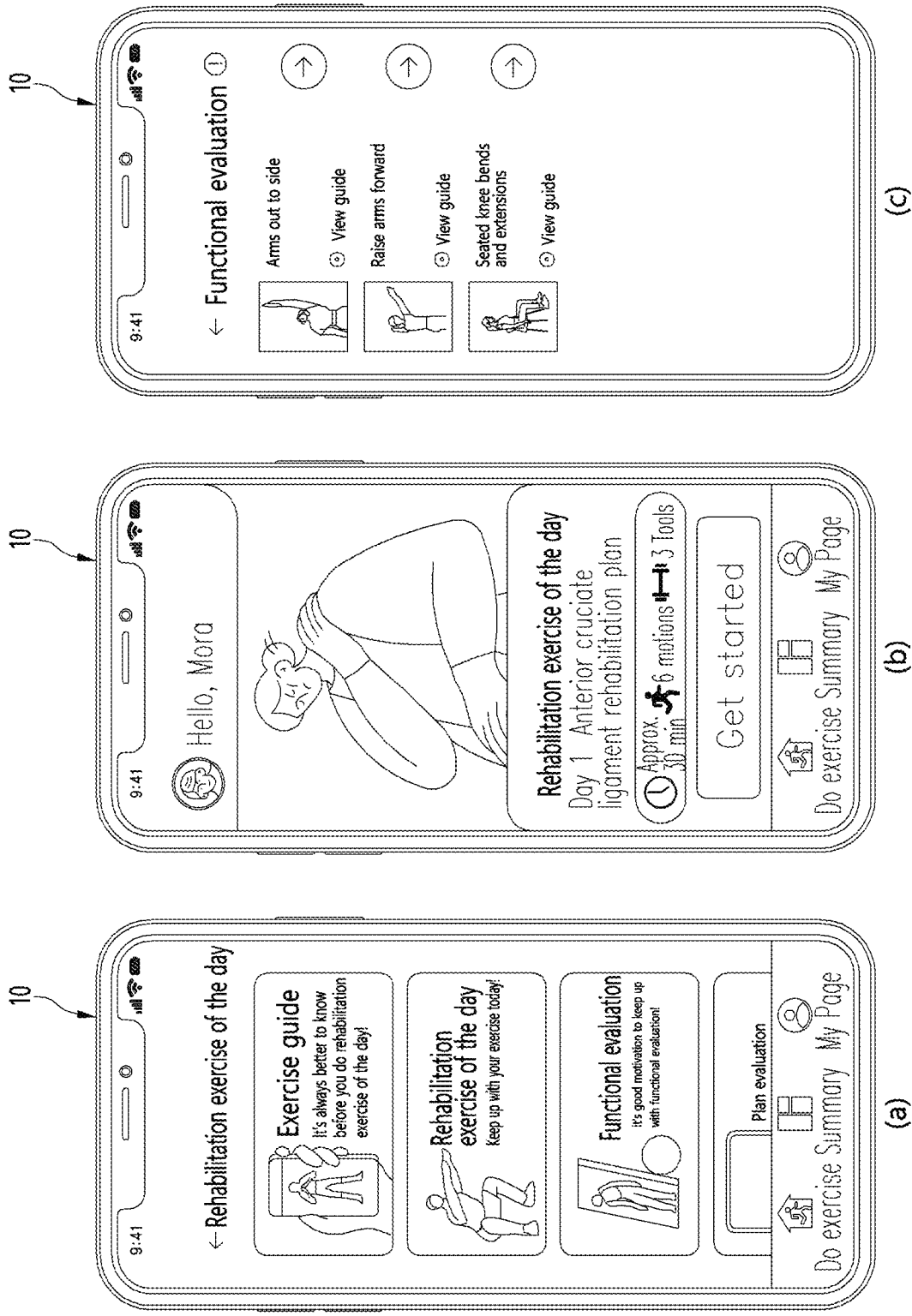
Figure 9C:
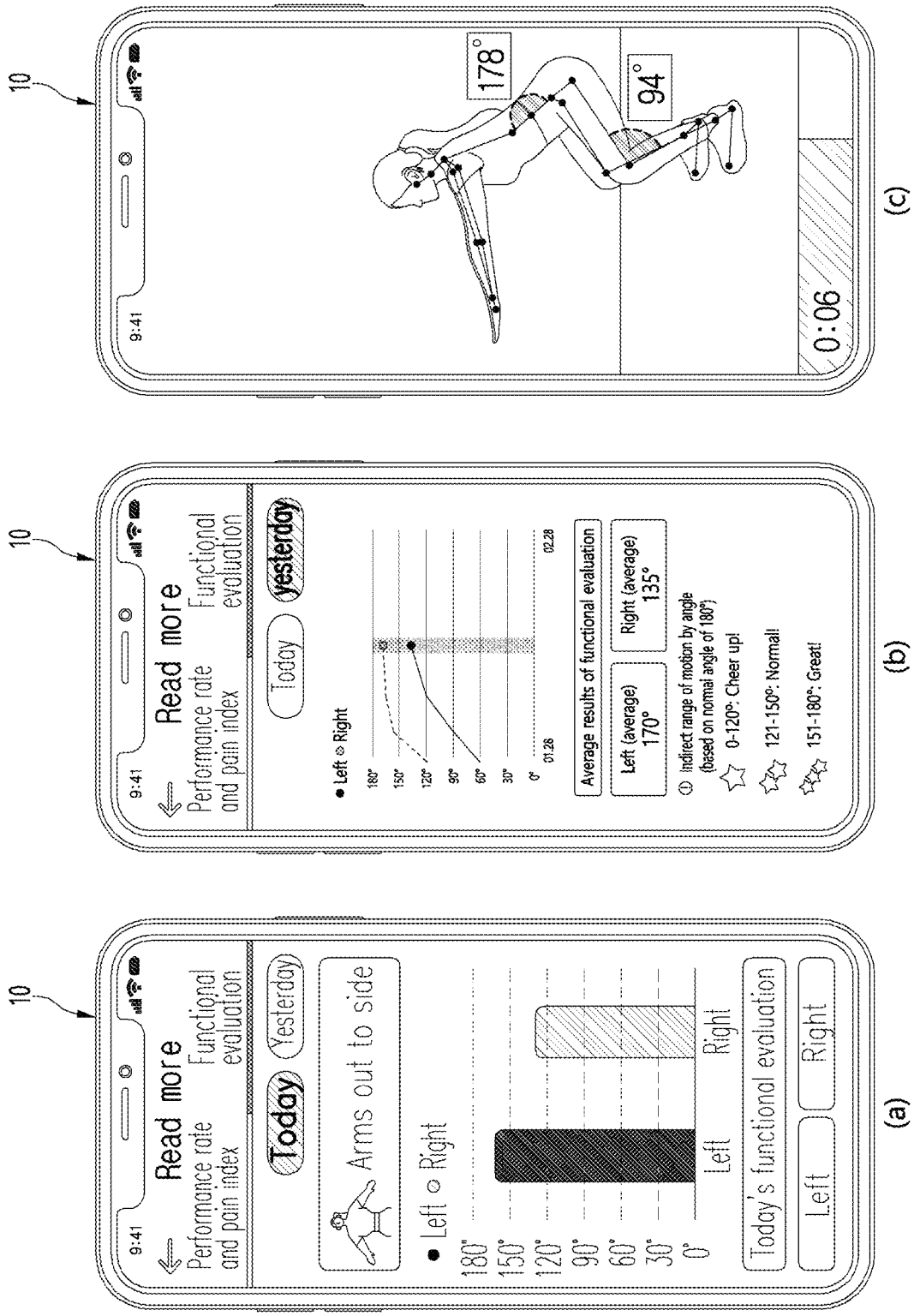

As illustrated in FIG. 8B, a training data set 400 in the present invention may be configured with a plurality of data groups 410 to 450, each corresponding to different information attributes 410a to 450a. The information contained in each of the plurality of data groups 410 to 450 may be configured by being extracted from the exercise image 300 including the subject U performing an exercise motion.

Here, the term "exercise image 300" refers to an image (or motion image) that photographs a process in which a user performs an exercise motion, as illustrated in FIG. 8A, which may include at least a portion of the body of the user U.

In the present invention, a user object included in an exercise image 300 may be described to be referred to as "subject U". In the present invention, the term "subject U" may mean a user or a portion of the body of the user who is exercising in the exercise image. Accordingly, the terms "subject" and "user" may be used interchangeably and may be described by assigning the same reference numeral "U".

Meanwhile, the "exercise image 300" described in the present invention may include an "exercise image targeted for analysis" and a "training target exercise image".

It may be understood that the "exercise image targeted for analysis" is an exercise image targeted for posture estimation analysis of the subject U, and the "training target exercise image" is an exercise image targeted for machine learning for the posture estimation model. Here, the pose estimation analysis may mean extracting keypoints from an image.

The training unit 51 may be configured to perform training for the posture estimation model based on the training target exercise image 300. The training unit 51 may train the posture estimation model using the training data.

As illustrated in (a) of FIG. 8B, the training unit 51 may detect the subject U in the training target exercise image 300, and extract various training data used for estimating the exercise posture from the detected subject U. This training data may be used interchangeably with the terms "information", "data", or "data value". Meanwhile, the extraction of training data may also be performed by means other than the training unit 51.

The training unit 51 may use an algorithm for various object detections to detect the subject U from the training target exercise image 300. For example, the training unit 51 may use an algorithm (weighted box fusion (WBF)) that ensembles a plurality of bounding boxes. However, it is obvious that the training unit 51 is not limited to the object detection algorithm described above, but may utilize various object detection algorithms that are capable of detecting an object corresponding to the subject U from the training target exercise image 300.

The training unit 51 may classify the extracted training data into one of the plurality of data groups 410 to 450, corresponding to each of the different plurality of information attributes 410a to 450a.

The different plurality of information attributes 410a to 450a described in the present invention may exist to be predefined, as illustrated in (b) of FIG. 8B. Further, the plurality of data groups 410 to 450 corresponding to each of the plurality of information attributes 410a to 450a may include training data corresponding to the predefined information attributes.

For example, i) the data group 410 corresponding to the first information attribute 410a may include the joint point position information on the subject U, and ii) the data group 420 corresponding to the second information attribute 420a may include information representing whether the joint point of the subject U is visible. Further, iii) the data group 430 corresponding to the third information attribute 430a may include information on the photographing direction of the subject U, iv) the data group 440 corresponding to the fourth information attribute 440a may include information on an exercise code that distinguishes an exercise motion (or an exercise type) performed by the subject U, and v) the data group 450 corresponding to the fifth information attribute 450a may include size and center position information on a bounding box for the subject U.

Here, the "joint point P1 or P2" may mean a joint of the user or an area corresponding to a joint of the subject U in the exercise image 300.

The training unit 51 may generate (constitute) a data set for the training target exercise image 300 by associating the plurality of data groups 410 to 450 extracted from the training target exercise image 300 with each other. Further, the training unit 51 may store the generated training data set 400 in the database 40. The database 40 may be built as a database 40 for the posture estimation model 52, based on the training data set 400 generated by the training unit 51 being stored therein.

Further, the training unit 51 may perform training for the posture estimation model 52 based on the training data set 400 that exists in the database 40. As described above, the training data set 400 may include the position information of the joint points.

The posture estimation model 52 is a posture estimation model trained using a training data set (Data set) including position information for a joint point, and may estimate an exercise posture of the subject U from an exercise image targeted for analysis.

Meanwhile, the posture estimation model 52 may extract keypoints corresponding to joint points of the subject from the exercise image 300 using the training data set 400 generated by the training unit 51, and at least one of the artificial intelligence motion analysis unit 122 or 212 and the rule-based motion analysis unit 123 or 213 may analyze an exercise motion of the subject in the exercise image 300 using the extracted keypoints.

The exercise posture of the subject U that may be estimated from the exercise image 300 targeted for analysis using the keypoints estimated from the posture estimation model 52 may vary. For example, at least one of the artificial intelligence motion analysis unit 122 or 212 and the rule-based motion analysis unit 123 or 213 may estimate and analyze information on at least one of i) a position of a joint point, ii) a range of motion of a joint of a joint point, iii) a movement path of a joint point, iv) a connection relationship between joint points, and v) a symmetry relationship of a joint point for the subject U.

In addition, the motion analysis unit 122 or 212 may perform an analysis of at least one of a distance of motion of a joint, a speed (or acceleration) of movement of a joint, a body balance of a subject (corresponding to a patient) included in an exercise image targeted for analysis, a body balance, and a body alignment state (e.g., an axial alignment state of a leg, a spinal alignment state, etc.) from the keypoints or image 300 extracted from the exercise image 300 targeted for analysis.

In the present invention, the posture estimation model 52 may also be configured to include the training unit 51. Further, in contrast, the training unit 51 may include the posture estimation model 52, in which case the posture estimation model 52 may be trained by the training unit 51 to perform a posture estimation function. Accordingly, in the present invention, the function performed by the posture estimation model 52 may be described interchangeably as being performed by the training unit 51.

Meanwhile, the user terminal 10 or 20 may be configured to perform a posture analysis result service that provides the user terminal 10 or 20 with an exercise motion analysis result (or an exercise motion analysis report) of a user, which is analyzed based on the keypoints extracted and estimated in the posture estimation model 52 (see FIG. 1).

Here, the user terminal 10 or 20 may be at least one of the patient terminal 10, the doctor terminal 20, or a terminal of a third party.

The system 1000 for providing exercise therapy may be configured to perform the communication with the user terminal 10 or 20. In the present invention, it may also be understood that the system 1000 for providing exercise therapy performs performing the communication is accomplished by the communication unit of the system 1000 for providing exercise therapy.

For example, the communication unit of the system 1000 for providing exercise therapy may be configured to perform the communication with the user terminal 10 or 20 using at least one of wireless LAN (WLAN), wireless-fidelity (Wi-Fi), wireless-fidelity (Wi-Fi) direct, digital living network alliance (DLNA), wireless broadband (WiBro), world interoperability for microwave access (WiMAX), high speed downlink packet access (HSDPA), high speed uplink packet access (HSUPA), long term evolution (LTE), long term evolution-advanced (LTE-A), fifth generation mobile telecommunication (5G), Bluetooth™ radio frequency identification (RFID), infrared communication (infrared data association (IrDA)), ultra-wideband (UWB), ZigBee, near field communication (NFC), Wi-Fi direct, or wireless universal serial bus (wireless USB) technologies.

Meanwhile, the user terminal 10 or 20 described in the present invention means an electronic device. For example, the electronic device may include at least one of a smart phone, a cell phone, a tablet PC, a kiosk, a computer, a laptop, a digital broadcasting terminal, a personal digital assistant (PDA), or a portable multimedia player (PMP). Further, the user terminal 10 or 20 may be an electronic device to which a user account is logged in, connected, or registered.

Here, the user account may mean an account registered in the system 1000 for providing exercise therapy according to the present invention. This user account may be understood as a user ID (identification or identification number).

Meanwhile, in the present invention, a process of receiving an exercise image from the user terminal 10 or 20 may be performed. The system 1000 for providing exercise therapy may receive, in communication with the user terminal 10 or 20, the exercise image 300, in which a user is photographed performing an exercise motion.

In this case, the exercise image 300 that the system 1000 for providing exercise therapy receives from the user terminal 10 or 20 may be understood as an exercise image targeted for an exercise motion analysis of the user.

The system 1000 for providing exercise therapy may receive an exercise image targeted for analysis from the user terminal 10 or 20 at various occasions and paths.

For example, as illustrated in FIG. 1, the system 1000 for providing exercise therapy may, based on a graphical object corresponding to "start an exercise" being selected from the user terminal 10 or 20, control a camera 201 provided on the user terminal 10 or 20 to be in an active state such that the camera 201 photographs an exercise image targeted for analysis. Further, the system 1000 for providing exercise therapy may receive the exercise image targeted for analysis that is photographed by the camera 201 from the user terminal 10 or 20 in real time or based on the completion of the user's exercise.

Next, in the present invention, a process of analyzing an exercise motion related to a specific exercise motion of a user included in an exercise image may proceed based on keypoints extracted from the posture estimation model trained using the training data set including the position information on the joint points.

When receiving the exercise image targeted for analysis from the user terminal 10 or 20, the training unit 51 may, based on the posture estimation model 52 trained using the training target exercise image 300, extract keypoints corresponding to joint points of the user U included in the exercise image targeted for analysis. Further, at least one of the artificial intelligence motion analysis unit 122 or 212 and the rule-based motion analysis unit 123 or 213 may analyze an exercise motion of the subject in the exercise image 300 using the extracted keypoints.

The posture estimation information of the user U estimated by the training unit 51 may include various information. For example, the training unit 51 may estimate i) the position information on the joint points P1 and P2 of the subject U, and ii) the information on the range of motion of the joint of the subject U (angle information).

Next, in the present invention, based on the completion of the analysis above, a process of providing an exercise motion analysis result of the user U related to a specific exercise motion to the user terminal 10 or 20 may proceed.

The system 1000 for providing exercise therapy may process an analysis result of an exercise motion of a user to generate an exercise motion analysis report. Further, the system 1000 for providing exercise therapy may provide the exercise motion analysis report on the user terminal 10 or 20.

For example, as illustrated in FIG. 1, the system 1000 for providing exercise therapy may provide joint point graphic objects corresponding to each of the joint points P1 and P2, at positions corresponding to the joint points P1 and P2 of the user U, in the exercise image of the user. Further, the system 1000 for providing exercise therapy may display joint range of motion information 221 of the specific joint point P1, around the specific joint point P1.

As described above, the system 1000 for providing exercise therapy according to the present invention may perform training for the posture estimation model 52 using the database 40 built based on the training target exercise image 300. Further, the posture estimation model 52 may be used to estimate the exercise posture of the user and perform a service of providing an exercise motion analysis result based on the estimated posture.

The information included in the analysis result may vary. For example, the analysis result may include analysis information on at least one of a range of motion of a joint, a distance of motion, a velocity (or acceleration) of movement of a joint, a body balance of a subject (corresponding to a patient) included in an exercise image targeted for analysis, a body balance, or a body alignment state (e.g., an axial alignment state of a leg, a spinal alignment state, etc.) analyzed from the extracted keypoints or image.

Further, the analysis information may further include a score, which may be an analysis score for an exercise motion (or posture) of the user. The analysis score may be calculated based on a variety of methods (e.g., a rule-based analysis based on a preset standard or an analysis by an artificial intelligence algorithm).

The training data set 400 extracted and generated from the training target exercise image 300 by the training unit 51 may be stored and exist in the database 40.

Hereinafter, the training data set 400 used to estimate an exercise posture of a user will be described in more detail.

As illustrated in FIG. 8A, the training data set 400 may be configured to include data associated with the subject U extracted from the training target exercise image 300.

The training unit 51 may extract data for the subject U from the training target exercise image 300 to configure a training data set 400.

This training data set 400 may be configured as a plurality of sub-data sets 401 to 403. In the present invention, it may be understood that the training data set 400 is a data set corresponding to an upper concept, and the sub-data sets 401 to 403 are data sets corresponding to a lower concept.

The training unit 51 may extract the data for the subject U from each of standard frames 301 to 306 selected based on the preset standard among the plurality of frames constituting the training target exercise image 300, and configure the sub-data sets 401 to 403.

The training unit 51 may select the standard frames 301 to 306 based on various standards. The training target exercise image 300 may be a motion image, or a plurality of still images.

When the training target exercise image 300 is a motion image, the training unit 51 may select the standard frames 301 to 306 based on a predetermined time interval T among the plurality of frames constituting the training target exercise image 300. In another example, the training unit 51 may, when the amount of change in the motion of the subject included in preceding and subsequent frames corresponds to a predetermined amount of change or more, select the preceding and subsequent frames as the standard frames 301 to 306.

The training data included in the training data set according to the present invention may be configured as training data extracted centered on the subject included in the training target exercise image, from each of the standard frames selected based on the preset standard among the plurality of frames constituting the training target exercise image.

Hereinafter, for convenience of description, the "training data set 400" and the "sub-data sets 401 to 403" are not separately distinguished, but the present invention will be described based on the "training data set 400". The information included in the training data set 400, described below, may be information included in the sub-data sets 401 to 403. In this case, the training data set 400 according to the present invention may be understood to include the plurality of sub-data sets 401 to 403 including information described below.

Meanwhile, as illustrated in (a) of FIG. 8B, the training data set 400 may be configured with a plurality of data groups 410 to 460, each corresponding to a different plurality of information attributes.

The training unit 51 may extract data corresponding to each of the plurality of information attributes from the training target exercise image, and classify (or match) data having the same information attributes of the extracted data into the same data group to generate the training data set 400.

Here, a plurality of information attributes 410a to 450a may be understood as a standard for distinguishing a type of information required for estimating the exercise posture of the subject U from the training target exercise image 300. As illustrated in (b) of FIG. 8B, in the present invention, the plurality of different information attributes (a first information attribute to a fifth information attribute, 410a to 450a) may exist to be predefined.

The training unit 51 may extract training data corresponding to each of the plurality of information attributes 410a to 450a from the training target exercise image, and classify the training data corresponding to the same information attribute into the same data group to generate the training data set 400.

Further, the training unit 51 may, based on an association between the plurality of information attributes 410a to 450a, specify an association for each group between the plurality of data groups 410 to 460, and perform training on the training data set 400 and the association for each group.

Hereinafter, the plurality of data groups and the association for each group will be described in detail.

Figure 8C:
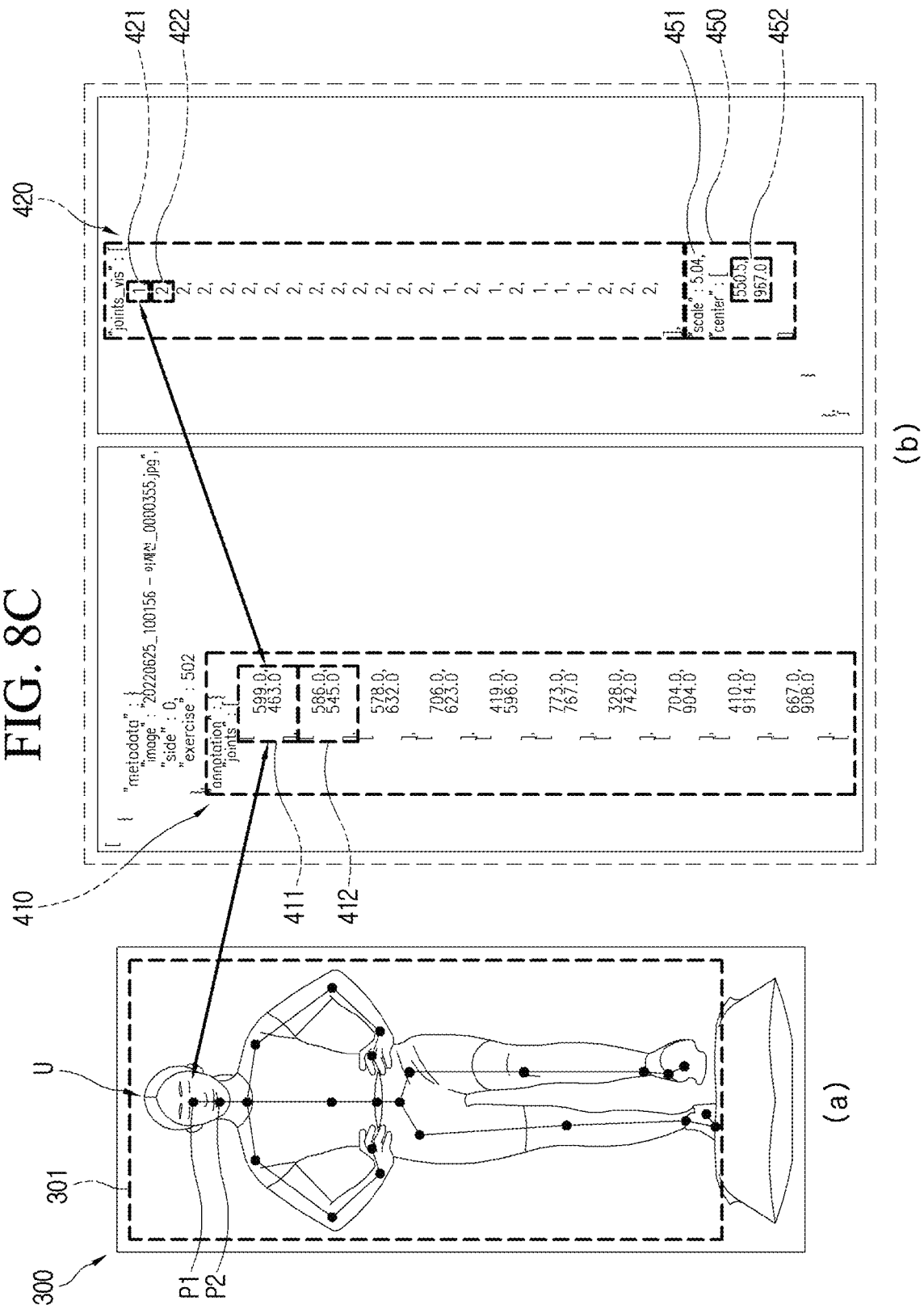

As illustrated in FIG. 8C, the first data group 410 of the plurality of data groups 410 to 450 may include position information 411 and 412 for the joint points P1 and P2 of the subject U included in the exercise image 300.

As illustrated in (a) of FIG. 8C, in the present invention, the joint points P1 and P2 may mean an area of the subject U corresponding to a joint of the user in the training target exercise image 300. Further, as illustrated in (b) of FIG. 8C, the position information 411 and 412 for joint points may be understood as a position of an area where the joint points P1 and P2 are positioned in the training target exercise image 300.

Meanwhile, the human body is made up of more than 200 bones, and a joint is a part where bone connects to each other, and the human body may consist of a plurality of joints.

In the training unit 51, the joint points of the plurality of joint points of the subject U, which are training targets, may exist to be predefined. That is, the "training target joint point" described in the present invention may be understood as a joint point predefined for training in the present invention among a plurality of joint points of the user.

Figure 8D:
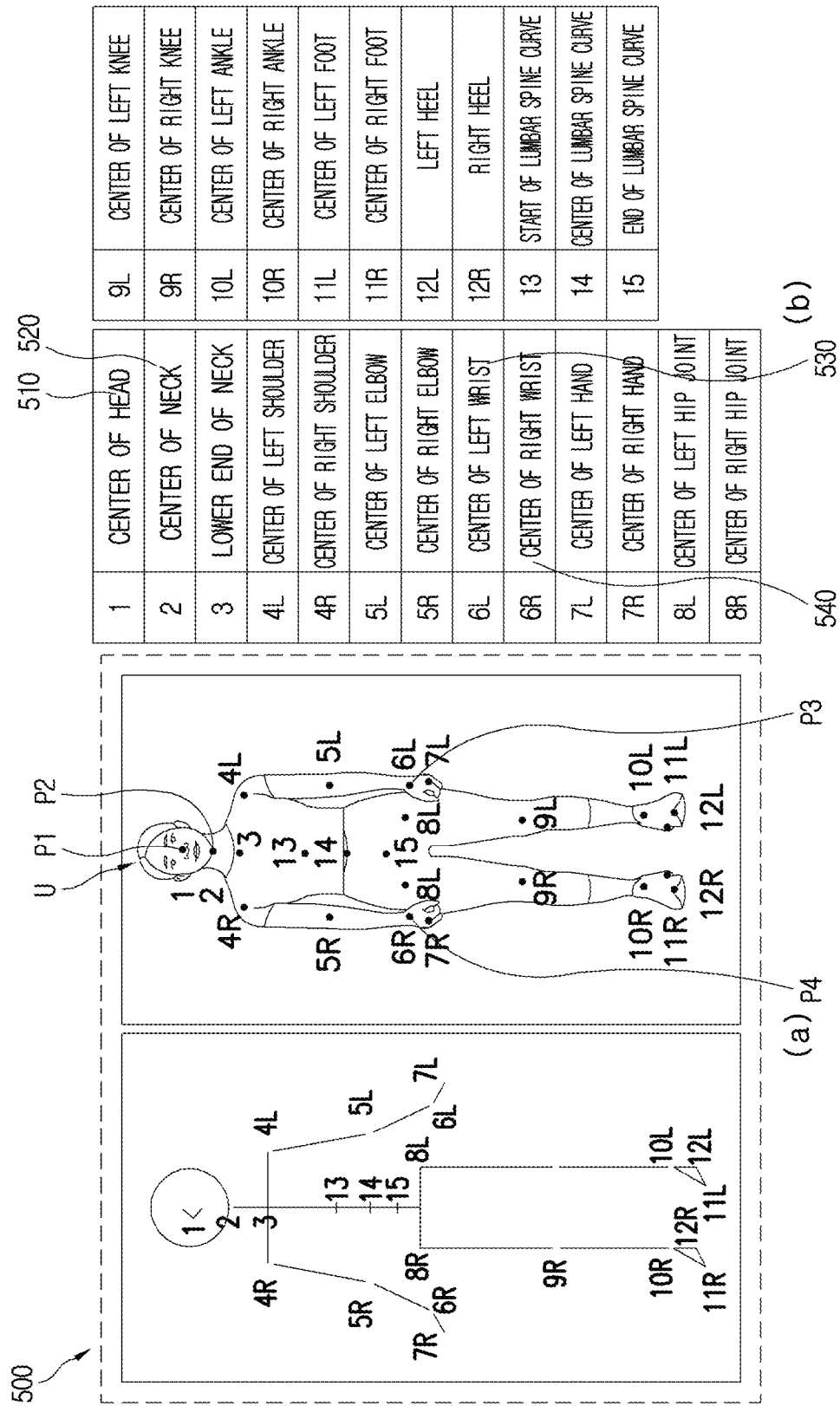

As illustrated in FIG. 8D, in the database 40, a training target joint point that is a training target of the posture estimation model among the plurality of joint points may be predesignated and exist as reference information 500. Further, there may be a predefined sequence of the plurality of training target joint points in the reference information 500.

A first training target joint point may be defined as a center of head. More specifically, the first training target joint point may be understood as a point that is inferred as (predicted as or corresponds to) a cervical 1 level.

A second training target joint point may be defined as a center of neck. More specifically, the second training target joint point is C3 to C4 level, which is a center of the neck lordotic curve, and may be understood as a midpoint in a middle level of levels 1 and 3 from the front.

A third training target joint point may be defined as a lower end of neck. More specifically, the third training target joint point is C7 to TI level, which may be understood as a midpoint of a line connecting both clavicle levels.

A fourth training target joint point may be defined as a center of shoulder. More specifically, the fourth training target joint point is a center of humerus head, which may be understood as a position that corresponds to a center of rotation of a continuous motion in a rotational motion in which the arm is abducted to a position that is a central axis of a shoulder joint rotation exercise. In an image that is not a continuous motion of the rotation exercise, a point corresponding to predicted position information of a center of shoulder may correspond to the fourth training target joint point. Further, the fourth training target joint point may exist at each of a center of left shoulder and a center of right shoulder.

A fifth training target joint point may be defined as a center of elbow. More specifically, the fifth training target joint point is a part corresponding to a center of the humerus medial-lateral epicondyle, which may be understood as a midpoint at an elbow level. The fifth training target joint point may exist at each of a center of left elbow and a center of right elbow.

A sixth training target joint point may be defined as a center of wrist. More specifically, the sixth training target joint point is a center of the radius-ulnar styloid process, which may be understood as a midpoint at a wrist level. The sixth training target joint point may exist at each of a center of left wrist and a center of right wrist.

A seventh training target joint point may be defined as a center of hand. More specifically, the seventh training target joint point may be understood as a point corresponding to the 3rd metacarpal head, and may exist at each of a center of left hand and a center of right hand.

An eighth training target joint point may be defined as a center of hip joint (a center of femoral head). More specifically, the eighth training target joint point is a position that is a central axis of a hip joint rotation exercise, which may be understood as a position corresponding to a rotational center of a continuous motion in which the leg is abducted. In an image that is not a continuous motion of the rotation exercise, a point corresponding to predicted position information of a center of hip joint may be understood as the eighth training target joint point. The eighth training target joint point may exist at each of a center of left hip joint and a center of right hip joint.

A ninth training target joint point may be understood as a center of knee. More specifically, the ninth training target joint point is a center of the femur medial-lateral epicondyle, which may be understood as a midpoint at a knee level. The ninth training target joint point may exist at each of a center of left knee and a center of right knee.

A tenth training target joint point may be defined as a center of ankle. More specifically, the tenth training target joint point is a center of the medial-lateral malleolus, which may be understood as a midpoint at an ankle level. The tenth training target joint point may exist at each of a center of left ankle and a center of right ankle.

An eleventh training target joint point may be defined as a center of foot. More specifically, the eleventh training target joint point is a point corresponding to the second metatarsal head, which may exist at each of a center of left foot and a center of right foot.

A twelfth training target joint point may be defined as a center of heel. More specifically, the twelfth training target joint point is a level at which the heel touches the floor, which may exist at each of left heel and right heel. The twelfth training target joint point may not be visible in the image when the subject U is standing perfectly front facing, but may be visible when the foot is even slightly deviated.

A thirteenth training target joint point may be defined as sup. end of lordosis. More specifically, the thirteenth training target joint point is a zypoid of sternum level, which is approximately 8-10T spine level, which may be understood as a midpoint at a middle level between an average level of both sides at level 4 and an average level of both sides at level 8.

A fourteenth training target joint point may be defined as a center of lordosis. More specifically, the fourteenth training target joint point is approximately L2-4 spine level, which may be understood as a midpoint at a middle level between level 13 and an average level of both sides at level 8.

A fifteenth training target joint point may be defined as sup. end of lordosis. More specifically, the fifteenth training target joint point is approximately S1-2 spine level, which may be understood as a midpoint at a middle level between level 14 and an average level of both sides at level 8.

Meanwhile, the first training target joint point P1 may be defined as the center of head 510, and the second training target joint point P2 may exist to be predefined as the center of neck 520. Further, a first sequence, which is the most prioritized sequence, may be defined at the first training target joint point P1, and a second sequence, which is prioritized lower than the first sequence, may be defined at the second training target joint point P2.

In this case, the sequence of training target joint points corresponding to each of the left and right sides of the subject U may be such that the training target joint point corresponding to a first side of the body (e.g., left) is prioritized over the training target joint point corresponding to a second side of the body (e.g., right). For example, a training target joint point P3 corresponding to a center of left wrist 530 may be matched with a sequence defined to be prioritized over a training target joint point P4 corresponding to a center of right shoulder 540.

The training unit 51 may extract coordinate information as the position information 411 and 412 of each of the plurality of predesignated training target joint points P1 and P2 from the training target exercise image 300.

The coordinate information may include at least one of two- or three-dimensional coordinates. When two-dimensional coordinate information is extracted, the training unit 120 may extract the x, y-axis coordinate information of each of the plurality of training target joint points P1 and P2 from the training target exercise image 300. In contrast, when two-dimensional coordinate information is extracted, the training unit 120 may extract the x, y, z-axis coordinate information of each of the plurality of training target joint points P1 and P2 from the training target exercise image 300.

The coordinate information may be extracted in a variety of ways. In particular, the coordinate information of the z-axis may be extracted from a camera (e.g., RGB camera) or various types of sensors (e.g., a distance measurement sensor). Further, the coordinate information of the z-axis may be extracted from the training target image 300 through various artificial intelligence algorithms. When the coordinate information of the z-axis is extracted by an artificial intelligence algorithm, it may be stated that the coordinate information of the z-axis is "estimated" or "predicted".

Meanwhile, the training unit 51 may, based on the position information 411 and 412 of each of the plurality of training target joint points P1 and P2 corresponding to the first information attribute 410*a*, classify the position information 411 and 412 into the first data group 410 to generate the first data group 410 and the training data set 400 including the first data group 410.

Taking the extraction of two-dimensional coordinate information (x, y coordination information) as an example, the training unit 121 may extract the position information 411, 412 of each of the plurality of training target joint points P1, P2 in the form of paired x-axis, y-axis coordinate information. The training unit 51 may extract the position information "436]" of the first training target joint point P1 and extract the position information "436]" of the second training target joint point P2. Further, the training unit 51 may generate the training data set 400 configured with the first data group 410 including "436]" and "436]".

The training unit 51 may, based on the position information 411 and 412 of the training target joint points P1 and P2 constituting the first data group 410, perform training to estimate the positions of the joint points P1 and P2 of the subject U included in the training target exercise image 300.

Meanwhile, as shown in (b) of FIG. 8C, the training unit 51 may, based on a predefined sequence between the plurality of training target joint points P1 and P2, sequentially arrange the position information 411 and 412 of each of the plurality of training target joint points P1 and P2 in the first data group 410 to configure (generate) the training data set 400.

As described above, there may be a predefined sequence of the plurality of training target joint points P1 and P2 in the database 40.

The training unit 51 may sequentially dispose the position information 411 and 412 of the plurality of training target joint points P1 and P2 in the first data group 410 according to a sequence corresponding to the training target joint points P1 and P2, with reference to the database 40, to generate the training data set 400. Further, the training data set 400 may be stored in the database 40 to build the database 40 for the posture estimation.

Specifically, as illustrated in (b) of FIG. 8C, the training unit 51 may arrange, in the first data group 410, the first position information 411 on the first training target joint point P1 corresponding to a first sequence in priority, and, following the first position information 411, the second position information 412 on the first training target joint point P2 corresponding to a second sequence.

Meanwhile, the training unit 51 may, based on whether the training target joint points P1 and P2 are visible in the exercise image 300, extract (or specify) the position information 411 and 412 of the training target joint points P1 and P2 according to a process of one of a first process and a second process.

In the present invention, whether the training target joint point is visible may be understood to mean whether the training target joint points P1 and P2 are visible in the training target exercise image 300.

In the present invention, a visible joint point in the training target exercise image may be referred to as a "training target visible joint point" and an invisible joint point in the training target exercise image may be referred to as a "training target invisible joint point".

The training unit 51 may judge that the training target joint point is visible in the training target exercise image 300 when the training target exercise image 300 includes a body part of the subject U corresponding to the training target joint points P1 and P2.

The training unit 51 may, based on the training target joint points P1 and P2 being visible in the training target exercise image 300, extract position information on an actual position where the training target joint points P1 and P2 are positioned from the training target exercise image 300 according to the first process.

In the present invention, the position information on the training target joint points P1 and P2 extracted according to the first process may be described to be referred to as "first type of information (first type of position information)" or "substantial position information".

In contrast, the training unit 51 may judge that the training target joint points P1 and P2 are invisible in the exercise image 300 when the training target exercise image 300 does not include a body part of the subject U corresponding to the training target joint points P1 and P2.

The training unit 51 may, based on the training target joint points P1 and P2 being invisible in the exercise image 300, predict an expected position of the training target joint points P1 and P2 according to the second process, and extract (or specify) predicted position information.

In the present invention, the position information on the training target joint points P1 and P2 extracted according to the second process may be described to be referred to as "second type of information (second type of position information)" or "predicted position information".

As such, in the present invention, the plurality of position information 411 and 412 included in the first data group 410 may have different extraction processes and type information defined depending on whether the plurality of training target joint points P1 and P2 are visible in the training target exercise image 300.

Meanwhile, the second process may include various data processing to extract (specify) the predicted position information on the invisible training target joint points P1 and P2 in the exercise image 300.

For example, the training unit 51 that extracts the predicted position information according to the second process may, based on an actual position information on the training target joint point visible in the exercise image 300, predict the predicted position information of the training target joint points P1 and P2 that are invisible in the exercise image 300.

In this case, the training unit 51 may assign a weight based on the association with the training target joint points P1 and P2 that are invisible in the exercise image 300 to the plurality of training target joint points P1 and P2 that are visible in the exercise image 300 to specify the predicted position information.

For example, the association between the training target joint points may be set to be higher as the sequence corresponding to the training target joint points P1 and P2 is closer. The association with the training target joint point corresponding to a third sequence may be set such that the training target joint point corresponding to the second sequence is higher than the training target joint point corresponding to the first sequence.

In another example, the association between the training target joint points P1 and P2 may be set to be the highest between the training target joint points P1 and P2 that exist corresponding to the left and right sides of the subject U, respectively. For example, the association with the training target joint point P3 corresponding to the center of left wrist may be set to be highest for the training target joint point P3 corresponding to the center of right wrist (sec (a) of FIG. 8C).

Further, the training unit 51 may, based on the motion information of the exercise motion performed by the subject U in the exercise image 300, extract the predicted position information of the training target joint points P1 and P2 that are invisible in the exercise image 300.

In the database 40, motion information including a movement path (e.g., movement position, movement direction) of the body (or joint point) according to the exercise motion may exist to be stored.

The training unit 51 may, with reference to the position information of the training target joint points P1 and P2 visible in the exercise image 300 and the motion information in the database 40, specify the predicted position information of the training target joints that are invisible in the exercise image 300.

Meanwhile, as illustrated in FIG. 8C, the second data group 420 of the plurality of data groups 410 to 450 may be configured with data values 421 and 422 representing whether the training target joint points P1 and P2 of the subject U included in the exercise image 300 are visible.

As illustrated in (b) of FIG. 8C, the data values of the data 421 and 422 included in the second data group 420 may be configured as one of a first data value (e.g., " ") and a second data value (e.g., " ") in response to whether the training target joint points P1 and P2 are visible.

The data having the first data value (e.g., " ") is data representing that the training target joint points P1, P2 are visible in the exercise image 300, which may be understood as information representing that the position information included in the first data group 410 is of a first type (actual position information).

The training unit 51 may extract the first type of position information (actual position information) of the training target joint point when the training target joint points P1 and P2 are visible in the exercise image 300. The training unit 51 may, based on the first type of position information (actual position information) extracted from the exercise image 300, generate (configure) the training data set 400 by including data having the first data value (e.g., " ") in the second data group 420.

In contrast, the second data value (e.g., " ") is data representing that the training target joint points P1, P2 are invisible in the exercise image 300, which may be understood as information representing that the position information included in the first data group 410 is of a second type (predicted position information).

The training unit 51 may extract (or specify) the second type of position information (actual position information) of the training target joint point when the training target joint point is invisible in the exercise image 300. The training unit 51 may, based on the second type of position information (predicted position information) extracted (or specified) from the exercise image 300, generate (configure) the training data set 400 by including the data having the second data value (e.g., " ") in the second data group 420.

Meanwhile, as illustrated in (b) of FIG. 8C, the training unit 51 may generate (configure) the training data set 400 by arranging the data (or data values, 421 and 422) included in the second data group 420 in the same sequence as the predefined sequence in which the position information 411 and 412 of each of the plurality of training target joint points P1 and P2 are arranged to represent whether each of the plurality of training target joint points is visible within the second data group 420.

The training unit 51 may, based on the predefined sequence between the plurality of training target joint points P1 and P2, sequentially arrange the data 421 and 422 representing whether each of the plurality of training target joint points is visible within the second data group 420.

For example, as illustrated in (b) of FIG. 8C, the training unit 51 may, based on the first training target joint point P1 being visible in the exercise image 300, arrange the data 421 having the first data value (e.g., " ") in the second data group 420 in the first sequence corresponding to the first training target joint point P1.

Further, although the second training target joint point P2 is illustrated as being visible in the exercise image 300 in (a) of FIG. 8C, assume that the second training target joint point P2 is invisible in the exercise image 300. The training unit 51 may, based on the second training target joint point P2 being visible in the exercise image 300, arrange the data 422 having the second data value (e.g., " ") in the second sequence corresponding to the second training target joint point P2.

Meanwhile, in the present invention, it may be understood that the definition of the type of position information included in the first data group 410 is made by the data value that the data included in the second data group 420 has.

As illustrated in (b) of FIG. 8C, assume that in the second data group 420, the data 421 arranged in the first sequence has the first data value (e.g., " ") and the data 422 arranged in the second sequence has the second data value (e.g., " ").

In the present invention, a type of the position information 411 arranged in the first sequence within the first data group 410 may be defined as the first type of position information (actual position information) based on the data 421 arranged in the first sequence within the second data group 420 having the first data value (e.g., " ").

In contrast, the type of the position information 411 arranged in the second sequence within the first data group 410 may be defined as the second type of position information (predicted position information) based on the data 422 arranged in the second sequence within the second data group 420 having the second data value (e.g., " ").

Meanwhile, the posture estimation model 52 according to the present invention may perform training by setting different training weights for the position information 411 and 412 of each of the plurality of training target joint points included in the first data group 410 based on the data value included in the second data group 420.

Specifically, when the data 421 arranged in the first sequence within the second data group 420 has the first data value (e.g., " "), the posture estimation model 52 may perform training by setting a first training weight for the position information 411 arranged in the first sequence within the first data group 410.

In contrast, when the data 422 arranged in the second sequence within the second data group 420 has the second data value (e.g., " "), the posture estimation model 52 may perform training by setting a second training weight for the position information 412 arranged in the second sequence within the first data group 410.

That is, the posture estimation model 52 may perform training by setting different training weights for the first type of position information (actual position information) and the second type of position information (predicted position information) based on the data value of the second data group 420.

In this case, the posture estimation model 52 may set the first training weight to be higher than the second training weight.

Meanwhile, as illustrated in FIG. 8B, the plurality of data groups 410 to 450 may further include a third data group 430 that includes information related to a photographing direction for the subject included in the exercise image 300. The third data group 430 may be configured with a data value representing a photographing direction in which the subject U included in the exercise image 300 is photographed.

Figure 8E:
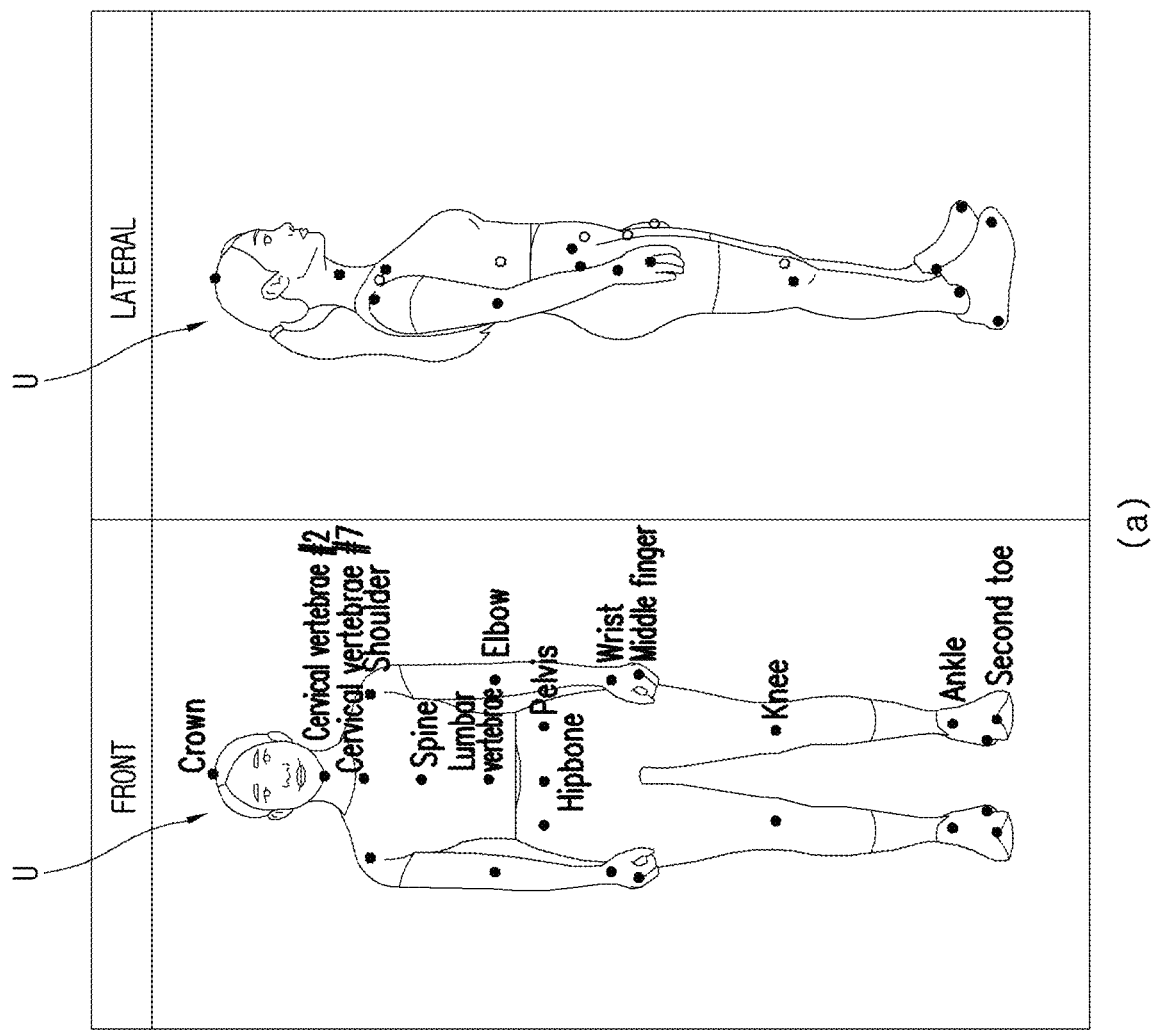

As illustrated in (a) of FIG. 8E, the subject U may be photographed from different photographing directions (e.g., "front" or "side").

Here, the term "photographing direction" may be understood as a direction of an axis of the camera (see reference numeral " " in FIG. 1) with respect to the subject U. Here, the camera 201 may be understood as the camera 201 that photographs the exercise image 300 including the subject U. The camera 201 may include the camera 201 provided on the user terminal 10 or 20.

The data values included in the third data group 430 illustrated in (b) of FIG. 8E may have different data values (e.g., " " or " ") in response to the photographing direction for the subject U. The data values included in the third data group may be configured to have different data values depending on the photographing direction of the subject, with respect to the camera that photographs the subject. Hereinafter, in order to avoid terminological confusion with the data value included in the second data group 420, the data value corresponding to the photographing direction will be described to be referred to as a "data object value".

The data having a first data object value (e.g., " ") may be understood as data in which the photographing direction for the training target exercise image 300 represents a first direction (e.g., a frontal direction) (sec (b) of FIG. 8E).

The training unit 51 may, based on the photographing direction for the subject U included in the training target exercise image 300 corresponding to the first direction (e.g., frontal direction), generate the training data set 400 by including data having the first data object value (e.g., " ") in the third data group 430.

In contrast, a second data object value (e.g., " ") may be understood as data in which the photographing direction for the exercise image 300 is a second direction (e.g., a lateral direction) that is different from the first direction (see (b) of FIG. 8E).

The training unit 51 may, based on the photographing direction for the subject U included in the exercise image 300 corresponding to the second direction (e.g., lateral direction), generate the training data set 400 by including data having the second data object value (e.g., " ") in the third data group 430.

Further, although not illustrated, a third data object value (e.g., " ") may be understood as data in which the photographing direction for the exercise image 300 represents a third direction (e.g., an oblique direction) that is different from the first and second directions.

The training unit 51 may, based on the photographing direction for the subject U included in the training target exercise image 300 corresponding to the third direction (e.g., an oblique direction), allow data having the third data object value (e.g., " ") to be included in the third data group 430 to be stored in the database 40.

Meanwhile, the first direction to the third direction described in the present invention may be understood as a case where an angle formed by the axis of the camera 201 and the subject U, with respect to a preset direction (e.g., clockwise direction), corresponds to each of a first range to a third range.

For example, the first direction may be understood that the angle formed by the axis of the camera 201 and the subject U corresponds to a range between a first angle and a second angle greater than the first angle. The second direction may be understood that the angle formed by the axis of the camera 201 and the subject U corresponds to a range between the second angle and a third angle greater than the second angle. Further, the third direction may be understood that the angle formed by the axis of the camera 201 and the subject U corresponds to a range between the second angle and a third angle greater than the second angle.

Meanwhile, the training unit 51 may configure the angle (or angle value) formed by the subject U and the axis of the camera 201 with respect to the preset direction (e.g., clockwise direction) as the data value of the data included in the third data group 430. For example, when the subject U and the axis of the camera 201 are perpendicular with respect to the clockwise direction, the training unit 51 may configure the data value of " " as the data of the third data group 430. Meanwhile, the training unit 51 may perform training for estimating the posture of the subject U in conjunction with the training data set 400, which has different photographing direction information included in the third data group 430.

For example, assume that there are a first training data set with a first data object value (e.g., " ") and a second training data set with a second data object value (e.g., " ") in the data included in the third data group 430. The training unit 51 may perform training for estimating the posture of the subject U in conjunction together with the position information of the first data group 410 included in the first data set and the position information of the first data group included in the second data set.

Meanwhile, when estimating the exercise posture of the subject U from an exercise image targeted for analysis photographed in the first direction, the training unit 51 may estimate the exercise posture of the subject U based on the posture estimation model performed training on the training target exercise image 300 photographed in the training target exercise image 300 photographed in the first direction.

The system 1000 for providing exercise therapy according to the present invention may analyze the exercise motion of the subject U based on the keypoints extracted from the posture estimation model trained using the training data set 400, which includes the photographing direction information (data object value or data value) corresponding to the photographing direction of the exercise image targeted for analysis.

Meanwhile, when estimating the exercise posture of the subject U from the exercise image targeted for analysis 300 photographed in the first direction, the motion analysis unit 120 or 210 may analyze the exercise motion of the subject U using the posture estimation information estimated from the posture estimation model trained on the training target exercise image 300 photographed in each of the first direction and the second direction.

That is, when the exercise motion of the subject U is photographed from the exercise image targeted for analysis 300 photographed in a first photographing direction, the motion analysis unit 120 or 210 may analyze the exercise motion of the subject U using the posture estimation information estimated from the posture estimation model that has performed training on the first training data set including data object values corresponding to the first photographing direction and the second training data set including data object values corresponding to a second photographing direction different from the first photographing direction. In this case, the posture estimation model 122 may correspond to a posture estimation model that has been performed training by setting a weight on the first training data set.

As such, the posture estimation model 52 may, according to the photographing direction of the subject included in the training target image, be trained through the training data set having different data values in consideration of the photographing direction of the subject. Further, the exercise motion analysis result of the user may be a result of analyzing a specific exercise motion of the user based on the posture estimation information extracted in consideration of the photographing direction of the user included in the exercise image in the posture estimation model.

Meanwhile, as illustrated in FIG. 8B, a fourth data group 440 of the plurality of data groups may include an exercise code matched to an exercise motion performed by the subject U included in the training target exercise image 300.

Figure 8F:
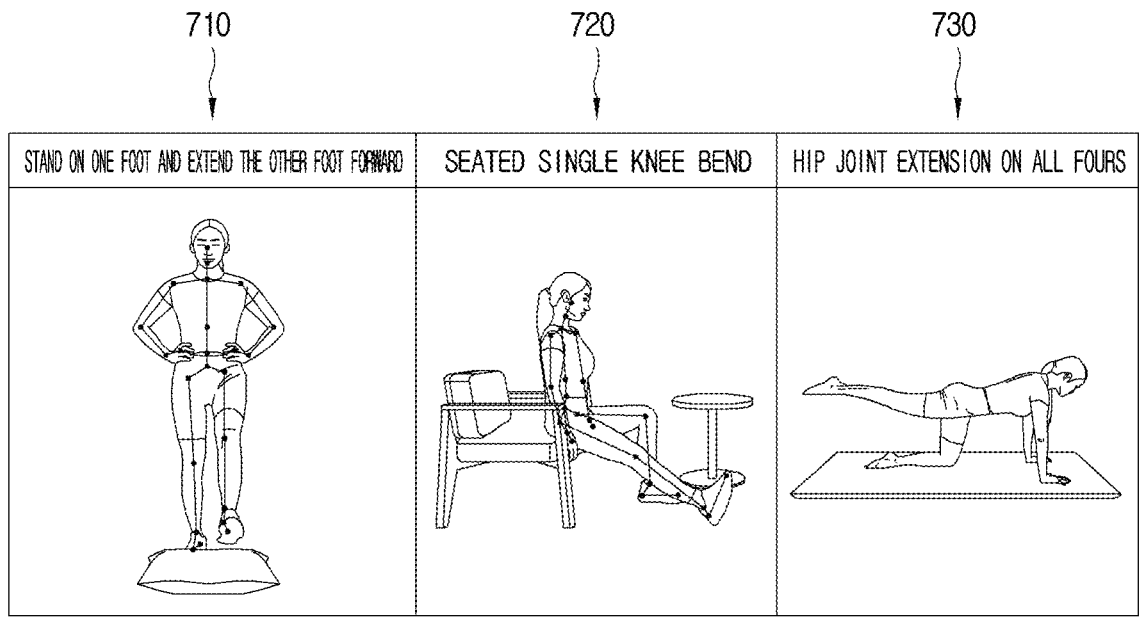

As illustrated in FIG. 8F, in the database 40, there may be different exercise codes (e.g., " " " " " ") matched to each of the different plurality of exercise motions 710, 720, and 730.

The term "exercise code" described in the present invention is a data value that distinguishes different exercise motions, which may be used interchangeably with the terms "exercise key," "motion code," and "motion key."

The training unit 51 may generate the training data set 400 by including, in the fourth data group 440, a specific exercise code (" ") matched to a specific exercise motion (e.g., "stand on one foot and extend the other foot forward", 710) performed by the subject U included in the training target exercise image 300.

The training unit 51 may associate the plurality of training data sets 400 including the same exercise codes with each other to perform training for the posture estimation.

For example, assume that there is a first training data set based on a first training target exercise image, and a second training data set based on a second training target exercise image 300. The training unit 51 may, based on the exercise codes (e.g., " ") included in the first training data set and the second training data set being the same, associate the first training data set and the second training data set with each other to perform training for the posture estimation.

These exercise codes may be included in the fourth data group 440, based on the exercise motion performed by the subject U being specified by at least one of the information received from the user terminal 10 or 20, the system administrator, or the training unit 51.

The training unit 51 may, based on the information received from the user terminals 10 or 20, specify the exercise motion performed by the subject U. For example, the training unit 51 may, based on a graphical object corresponding to "start an exercise" being selected from the user terminal 10 or 20, control a camera 201 provided on the user terminal 10 or 20 to be in an active state such that the camera 201 photographs an exercise image.

In this case, the graphic object may correspond to a specific exercise motion, and the training unit 51 may judge that the subject U included in the exercise image 300 received from the user terminal 10 or 20 has performed the specific exercise motion.

Further, the training unit 51 may, based on information input by the system administrator, specify the exercise motion performed by the subject U.

Further, the training unit 51 may, based on the position information of the training target joint of the subject U included in the exercise image 300, specify the exercise motion performed by the subject U. In this case, with reference to the motion information for the exercise motion stored in the database 40, the exercise motion performed by the subject U may be specified.

Meanwhile, the training unit 51 may match the plurality of training data sets 400 including the same exercise code to each other, on the basis of the exercise code included in the fourth data group 440, to be stored in the database 40.

In this case, the training unit 51 may, on the basis of the training code, divide the memory (or memory space) of the database 40 to be allocated. In the present invention, the dividing of the memory (or memory space) of the database 40 may be understood as generating a folder on the database 40 on the basis of the exercise code. Further, the training unit 51 may store the training data set 400 including a specific exercise code in a folder corresponding to the specific exercise code.

Meanwhile, the motion analysis unit 120 or 210 may analyze an exercise motion using the posture estimation information estimated from the posture estimation model trained using a training data set including the exercise code corresponding to the specific exercise motion performed by the subject U in the exercise image targeted for analysis.

Further, the motion analysis units 120 and 210 may estimate the exercise motion of the subject U for the specific exercise motion using the posture estimation information estimated from the posture estimation model trained based on the training target exercise image 300 related to the same specific exercise motion as the subject U included in the analysis exercise target.

Meanwhile, as illustrated in FIG. 8c, a fifth data group 450 of the plurality of data groups 410 to 450 may include size information 451 on the bounding box 301 for the subject U included in the training target exercise image 300, and position information 452 centered on the bounding box 301.

In the present invention, the term "size information" of the bounding box 301 may be used interchangeably with the term "scale".

The training unit 51 may extract the size information 451 on the bounding box 301 corresponding to the subject U detected in the training target exercise image 300, extract center position information 452 on the bounding box 301, and generate the training data set 400 by including the extracted size and center position information in the fifth data group 450.

As described above, the training unit 51 may use an algorithm for various object detections to detect the subject U from the training target exercise image 300. For example, the training unit 51 may use an algorithm (weighted box fusion (WBF)) that ensembles a plurality of bounding boxes. However, it is obvious that the training unit 51 is not limited to the object detection algorithm described above, but may utilize various object detection algorithms that are capable of detecting an object corresponding to the subject U from the training target exercise image 300.

The training unit 51 may, based on the object detection algorithm, extract the size information 451 and the center position information 452 on the bounding box corresponding to the subject U from the training target image 300, and include the size information 451 and the center position information 452 in the fifth data group 450 to generate the training data set 400.

In this case, the training unit 51 may extract the center position information 452 on the bounding box 301 in the form of paired x-axis and y-axis coordinate information.

Meanwhile, the training unit 51 may configure the training data set 400 by including image identification information on the training target exercise image 300.

Here, the term "image identification information" refers to information for identifying the image 300 from which the information included in the training data set is extracted, which may include, for example, filename information, file format type information (or extension information, e.g., " " " ") of the training target exercise image 300.

In the present invention, the image identification information may be referred to as a sixth data group corresponding to a sixth information attribute.

The training unit 51 may generate the training data set 400 by including the sixth data group configured with the image identification information.

Meanwhile, in the present invention, an exercise motion analysis result may be provided to the patient terminal 10 on the basis of completing an analysis of the exercise motion of the patient based on the motion analysis unit 120 or 210. As illustrated in FIGS. 9A, 9B, and 9C, the exercise motion analysis results may be provided through the exercise therapy application 100 installed on the patient terminal 10.

As illustrated in (a) of FIG. 9A, the exercise therapy application 100 may provide, on the patient terminal 10, a service page configured to be accessible for each of a plurality of services provided in the present invention. For example, the service page may be configured to be accessible to at least one of i) an exercise guide page associated with a function of providing exercise guide information for an exercise plan allocated to the patient account, ii) an exercise page related to performing an exercise plan allocated to the patient account (see (b) of FIG. 9A), iii) a functional evaluation page associated with a functional evaluation (sec (c) of FIG. 9A), or iv) a plan evaluation page associated with an exercise plan evaluation function.

Further, as illustrated in FIG. 9B, the exercise therapy application 100 may provide, on the patient terminal 10, an exercise report page that provides an exercise report based on an exercise motion analysis result and an exercise performance result. For example, the exercise report page may include at least one of exercise performance rate information (see (a) and (b) of FIG. 9B) or exercise plan difficulty information (sec (c) of FIG. 9B).

Further, as illustrated in FIG. 9C, the exercise therapy application 100 may provide, on the patient terminal 10, the exercise motion analysis result of the patient.

As illustrated in (a) of FIG. 9C, the exercise therapy application 100 may provide, on the patient terminal 10, a plurality of exercise motion analysis information for each joint point of the subject U performing a specific prescribed exercise (e.g., "arms out to side"). For example, the exercise therapy application 100 may provide, on the patient terminal 10, a graph of a range of motion of a joint for a joint point positioned on a first side (e.g., left) of the patient and a range of motion of a joint for a joint point positioned on a second side (e.g., right) of the patient.

As illustrated in (b) of FIG. 9C, the exercise therapy application 100 may provide an exercise motion analysis result of the patient who performed a prescribed exercise according to an exercise plan over a period of time, on a daily basis. For example, the exercise therapy application 100 may provide joint range of motion information corresponding to a first exercise day and joint range of motion information corresponding to a second exercise day. Further, the exercise therapy application 100 may provide an average range of motion of a joint on the first exercise day and the second exercise day.

As illustrated in (c) of FIG. 9C, the exercise therapy application 100 may render graphic objects corresponding to the keypoints P1 and P2 on the exercise image 300 and provide the graphic objects on the patient terminal 10. In this case, the exercise therapy application 100 may provide the joint range of motion information (angle information) of the patient together.

On the other hand, the system 1000 for providing exercise therapy according to the present invention may also provide the exercise motion analysis result provided to the patient terminal 10 to the doctor terminal 20 such that the doctor may perform monitoring on the performance of the exercise plan of the patient.

Figure 10:
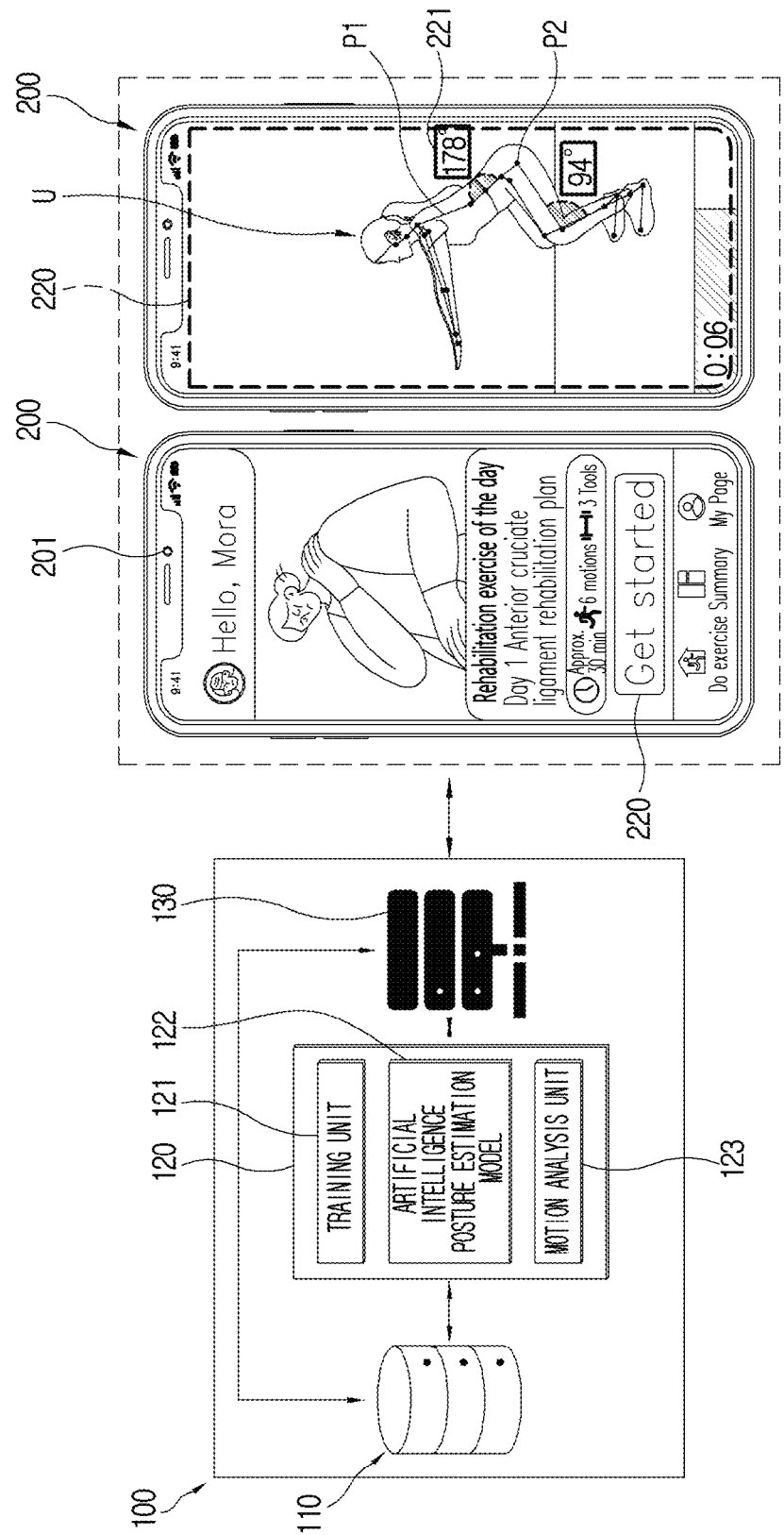
FIG. 10 is a conceptual view for describing a system of estimating exercise posture and analyzing an exercise motion according to the present invention.

As illustrated in FIG. 10, the exercise motion analysis system 100 according to the present invention may be configured to include at least one configuration of the database 110, the motion analysis server 120, or a service server 130. The database 110 is storage where the training data set is stored, which may be provided in the exercise motion analysis system 100 itself according to the present invention or may be configured as an external storage (or external DB). It may be understood that the database 110 according to the present invention is sufficient to be the space in which the training data set is stored, and is not limited by a physical space.

In the database 110, training data for training the posture estimation model 122 (or artificial intelligence posture estimation model) may be stored as a training data set.

As illustrated in FIG. 8B, a training data set 400 in the present invention may be configured with a plurality of data groups 410 to 450, each corresponding to different information attributes 410a to 450a. The information contained in each of the plurality of data groups 410 to 450 may be configured by being extracted from the exercise image 300 including the subject U performing an exercise motion.

Here, the term "exercise image 300" refers to an image (or motion image) that photographs (includes) a process in which a user performs an exercise motion, as illustrated in FIG. 8A, which may include at least a portion of the body of the user U.

In the present invention, a user object included in an exercise image 300 may be described to be referred to as "subject U". In the present invention, the term "subject U" may mean a user or a portion of the body of the user who is exercising in the exercise image. Accordingly, the terms "subject" and "user" may be used interchangeably and may be described by assigning the same reference numeral "U".

Meanwhile, the "exercise image 300" described in the present invention may include an "exercise image targeted for analysis" and a "training target exercise image".

It may be understood that the "exercise image targeted for analysis" is an exercise image targeted for posture estimation analysis of the subject U, and the "training target exercise image" is an exercise image targeted for machine learning for the posture estimation model.

Meanwhile, in the present invention, the motion analysis server 120 may include at least one configuration of the training unit 121, the posture estimation model 122, or the motion analysis unit 123. The motion analysis server 120 may be provided inside the exercise motion analysis system 100 according to the present invention, or may be configured as an external server. That is, the motion analysis server according to the present invention is to perform a function of performing at least one of training for posture estimation, posture estimation, or exercise motion analysis, which may be understood to have no constraints on a physical space.

The training unit 121 may be configured to perform training for the posture estimation model based on the training target exercise image 300. The training unit 121 may train the posture estimation model using the training data. Further, the training unit 121 may train the motion analysis unit 123.

As illustrated in (a) of FIG. 8B, the training unit 121 may detect the subject U in the training target exercise image 300, and extract various training data used for estimating the exercise posture from the detected subject U. This training data may be used interchangeably with the terms "information", "data", or "data value". Meanwhile, the extraction of training data may also be performed by means other than the training unit 121.

The training unit 121 may use an algorithm for various object detections to detect the subject U from the training target exercise image 300. For example, the training unit 121 may use an algorithm (weighted box fusion (WBF)) that ensembles a plurality of bounding boxes. However, it is obvious that the training unit 121 is not limited to the object detection algorithm described above, but may utilize various object detection algorithms that are capable of detecting an object corresponding to the subject U from the training target exercise image 300.

The training unit 121 may classify the extracted training data into one of the plurality of data groups 410 to 450, corresponding to each of the different plurality of information attributes 410a to 450a.

The different plurality of information attributes 410a to 450a described in the present invention may exist to be predefined, as illustrated in (b) of FIG. 8B. Further, the plurality of data groups 410 to 450 corresponding to each of the plurality of information attributes 410a to 450a may include training data corresponding to the predefined information attributes.

For example, i) the data group 410 corresponding to the first information attribute 410a may include the joint point position information on the subject U, and ii) the data group 420 corresponding to the second information attribute 420a may include information representing whether the joint point of the subject U is visible. Further, iii) the data group 430 corresponding to the third information attribute 430a may include information on the photographing direction of the subject U, iv) the data group 440 corresponding to the fourth information attribute 440a may include information on an exercise code that distinguishes an exercise motion (or an exercise type) performed by the subject U, and v) the data group 450 corresponding to the fifth information attribute 450a may include size and center position information on a bounding box for the subject U.

Here, the "joint point P1 or P2" may mean a joint of the user or an area corresponding to a joint of the subject U in the exercise image 300.

The training unit 121 may generate (constitute) a data set for the training target exercise image 300 by associating the plurality of data groups 410 to 450 extracted from the training target exercise image 300 with each other. Further, the training unit 121 may store the generated training data set 400 in the database 10. The database 10 may be built as the database 110 for the posture estimation model 122, based on the training data set 400 generated by the training unit 121 being stored therein.

Further, the training unit 121 may perform training for the posture estimation model 122 based on the training data set 400 that exists in the database 110. As described above, the training data set 400 may include the position information of the joint points.

The posture estimation model 122 is a posture estimation model trained using a training data set including position information for a joint point. The posture estimation model 122 may extract (or specify) a joint point of the subject U from the exercise image targeted for analysis, and further extract the position information of the joint point. That is, the posture estimation model 122 may be configured to extract or estimate a keypoint corresponding to a joint point of the subject U included in the exercise image targeted for analysis. In the present invention, for convenience of description, a process of extracting or estimating a joint point (or keypoint) may be collectively referred to as an "estimation".

The motion analysis unit 123 may analyze (or estimate) the exercise motion of the subject U from the exercise image targeted for analysis using the position information (or keypoint) of the joint point of the subject U extracted from the posture estimation model 122. The motion analysis unit 123 may also be referred to as an "artificial intelligence motion analysis model" or "motion analysis model".

The motion analysis unit 123 may perform a motion analysis using at least one of training data generated by the training unit 121 or the posture estimation information estimated from the posture estimation model 122 trained by the training data. It is obvious that the motion analysis unit 123 may be configured to be trained based on the training data generated by the training unit 121.

In the present invention, the "posture estimation" means extracting position information of a joint point or a keypoint corresponding to a joint point from an image, and the "motion analysis" means analyzing a motion using the extracted position information or keypoint.

Meanwhile, the motion analysis information on the subject U that the motion analysis unit 123 may analyze from the exercise image targeted for analysis 300 may vary. For example, the motion analysis unit 123 may estimate and analyze information on at least one of i) a range of motion of a joint for a joint point, ii) a movement path of a joint point, iii) a connection relationship between joint points, or iv) a symmetry relationship of a joint point for the subject U, from the joint points extracted or estimated by the posture estimation model 122.

In addition, the motion analysis unit 123 may perform an analysis of at least one of a distance of motion of a joint, a speed (or acceleration) of movement of a joint, a body balance of a subject (corresponding to a patient) included in an exercise image targeted for analysis, a body balance, and a body alignment state (e.g., an axial alignment state of a leg, a spinal alignment state, etc.) from the keypoints or image 300 extracted from the exercise image 300 targeted for analysis.

In the present invention, the posture estimation model 122 may also be configured to include the training unit 121. Further, in contrast, the training unit 121 may include the posture estimation model 122, in which case the posture estimation model 122 may be trained by the training unit 121 to perform a posture estimation function. Accordingly, in the present invention, the function performed by the posture estimation model 122 may be described interchangeably as being performed by the training unit 121.

Meanwhile, the service server 130 may, through the motion analysis unit 123 that performs an analysis using the keypoints estimated in the posture estimation model 122, be configured to perform to provide a motion analysis result service that provides the exercise motion analysis result (or the exercise motion analysis report 220) of the user to a user terminal 200 (see FIG. 10).

The service server 130 may be configured to perform the communication with the user terminal 200. In the present invention, it may also be understood that the service server 130 performs performing the communication is accomplished by the communication unit of the service server 130.

For example, the communication unit of the service server 130 may be configured to perform the communication with the user terminal 200 using at least one of wireless LAN (WLAN), wireless-fidelity (Wi-Fi), wireless-fidelity (Wi-Fi) direct, digital living network alliance (DLNA), wireless broadband (WiBro), world interoperability for microwave access (WiMAX), high speed downlink packet access (HSDPA), high speed uplink packet access (HSUPA), long term evolution (LTE), long term evolution-advanced (LTE-A), fifth generation mobile telecommunication (5G), Bluetooth™ radio frequency identification (RFID), infrared communication (infrared data association (IrDA)), ultra-wideband (UWB), ZigBee, near field communication (NFC), Wi-Fi direct, or wireless universal serial bus (wireless USB) technologies.

Meanwhile, the user terminal 200 described in the present invention means an electronic device. For example, the electronic device may include at least one of a smart phone, a cell phone, a tablet PC, a kiosk, a computer, a laptop, a digital broadcasting terminal, a personal digital assistant (PDA), or a portable multimedia player (PMP). Further, the user terminal 200 may be an electronic device to which a user account is logged in, connected, or registered.

Here, the user account may mean an account registered in the exercise motion analysis system 100 according to the present invention. This user account may be understood as a user ID (identification or identification number).

Figure 11:
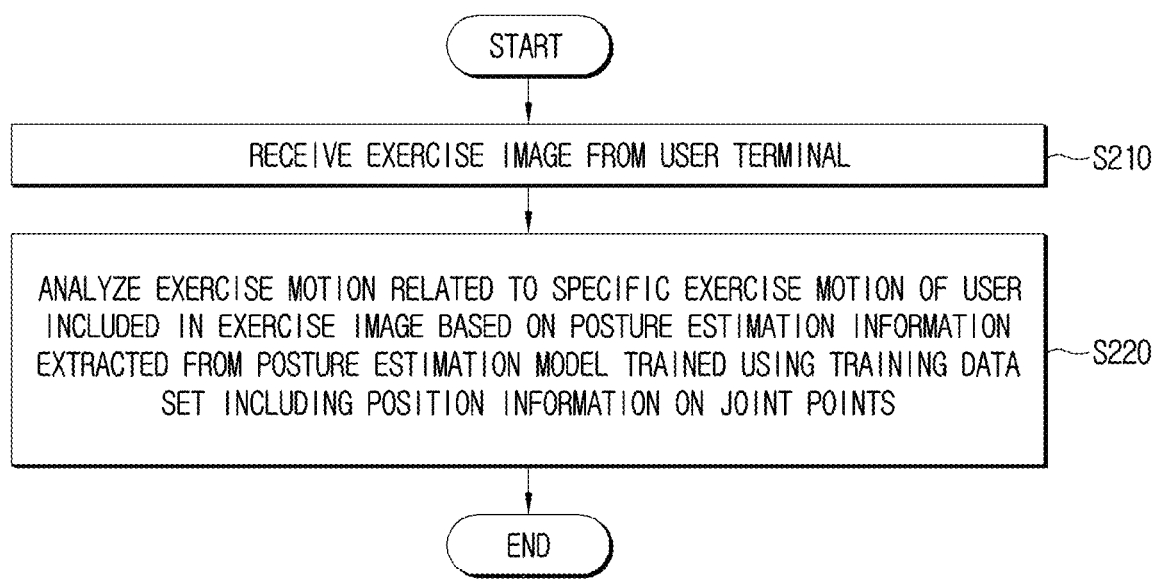
FIG. 11 is a flowchart for describing a method of estimating exercise posture and analyzing an exercise motion according to the present invention.

Meanwhile, in the present invention, a process of receiving an exercise image from the user terminal 200 may be performed (S210, see FIG. 11). The service server 130 may receive, in communication with the user terminal 200, the exercise image 300, in which a user is photographed performing an exercise motion.

In this case, the exercise image 300 that the service server 130 receives from the user terminal 200 may be understood as an exercise image targeted for an exercise motion analysis of the user. Meanwhile, the training unit 121 may not only estimate the posture to extract the keypoints for the joint points of the user using the exercise image targeted for analysis, but also perform training for the posture estimation model using the training target exercise image 300.

The service server 130 may receive an exercise image targeted for analysis from the user terminal 200 at various occasions and paths.

For example, as illustrated in FIG. 10, the service server 130 may, based on a graphical object 210 corresponding to "start an exercise" being selected from the user terminal 200, control a camera 201 provided on the user terminal 200 to be in an active state such that the camera 201 photographs an exercise image targeted for analysis. Further, the service server 130 may receive the exercise image targeted for analysis that is photographed by the camera 201 from the user terminal 200 in real time or based on the completion of the user's exercise.

Next, in the present invention, a process of analyzing an exercise motion related to a specific exercise motion of a user included in an exercise image may proceed based on the posture estimation information extracted from the posture estimation model trained using the training data set including the position information on the joint points (S220, see FIG. 11).

When receiving the exercise image targeted for analysis from the user terminal 200, the motion analysis unit 123 may estimate the exercise motion of the user U included in the exercise image targeted for analysis using the posture estimation information extracted based on the posture estimation model 122 trained using the training target exercise image 300. Here, the posture estimation information may include at least one of information on the joint point (P1, P2, or keypoint) or the position information thereof.

The exercise motion of the user U analyzed by the motion analysis unit 123 may include a variety of information. For example, the motion analysis unit 123 may estimate the joint range of motion information (angle information) of the subject U based on the position information of the joint points P1 and P2.

Next, in the present invention, based on the completion of the analysis above, a process of providing an exercise motion analysis result of the user U related to a specific exercise motion to the user terminal 200 may proceed (S230, see FIG. 11).

The service server 130 may process an analysis result of an exercise motion of a user to generate an exercise motion analysis report. Further, the service server 130 may provide the exercise motion analysis report on the user terminal 200.

For example, as illustrated in FIG. 10, the service server 130 may render and provide joint point graphic objects corresponding to each of the joint points P1 and P2, to positions corresponding to the joint points P1 and P2 of the user U, in the exercise image of the user. Further, the service server 130 may display joint range of motion information 221 of the specific joint point P1, around the specific joint point P1.

The exercise motion analysis system 100 according to the present invention may perform training for the posture estimation model 122 using the database 110 built based on the training target exercise image 300. Further, the motion analysis unit 123 analyzes the exercise motion of the user based on the posture estimation information obtained using the posture estimation model 122, and as a result, the service of providing the exercise motion analysis result may be performed.

The information included in the analysis result may vary. For example, the analysis result may include analysis information on at least one of a range of motion of a joint, a distance of motion, a velocity (or acceleration) of movement of a joint, a body balance of a subject (corresponding to a patient) included in an exercise image targeted for analysis, a body balance, or a body alignment state (e.g., an axial alignment state of a leg, a spinal alignment state, etc.) analyzed from the extracted keypoints or image.

Further, the analysis information may further include a score, which may be an analysis score for an exercise motion (or posture) of the user. The analysis score may be calculated based on a variety of methods (e.g., a rule-based analysis based on a preset standard or an analysis by an artificial intelligence algorithm).

The training data set 400 extracted and generated from the training target exercise image 300 by the training unit 121 may be stored and exist in the database 110.

Hereinafter, the training data set 400 used to estimate an exercise posture of a user will be described in more detail.

Meanwhile, in the present invention, the exercise motion analysis result may be provided to the user terminal 200 on the basis of the completion of an analysis of the exercise motion of the user included in the exercise image targeted for analysis through the posture estimation information extracted based on the posture estimation model 122.

Figure 12:
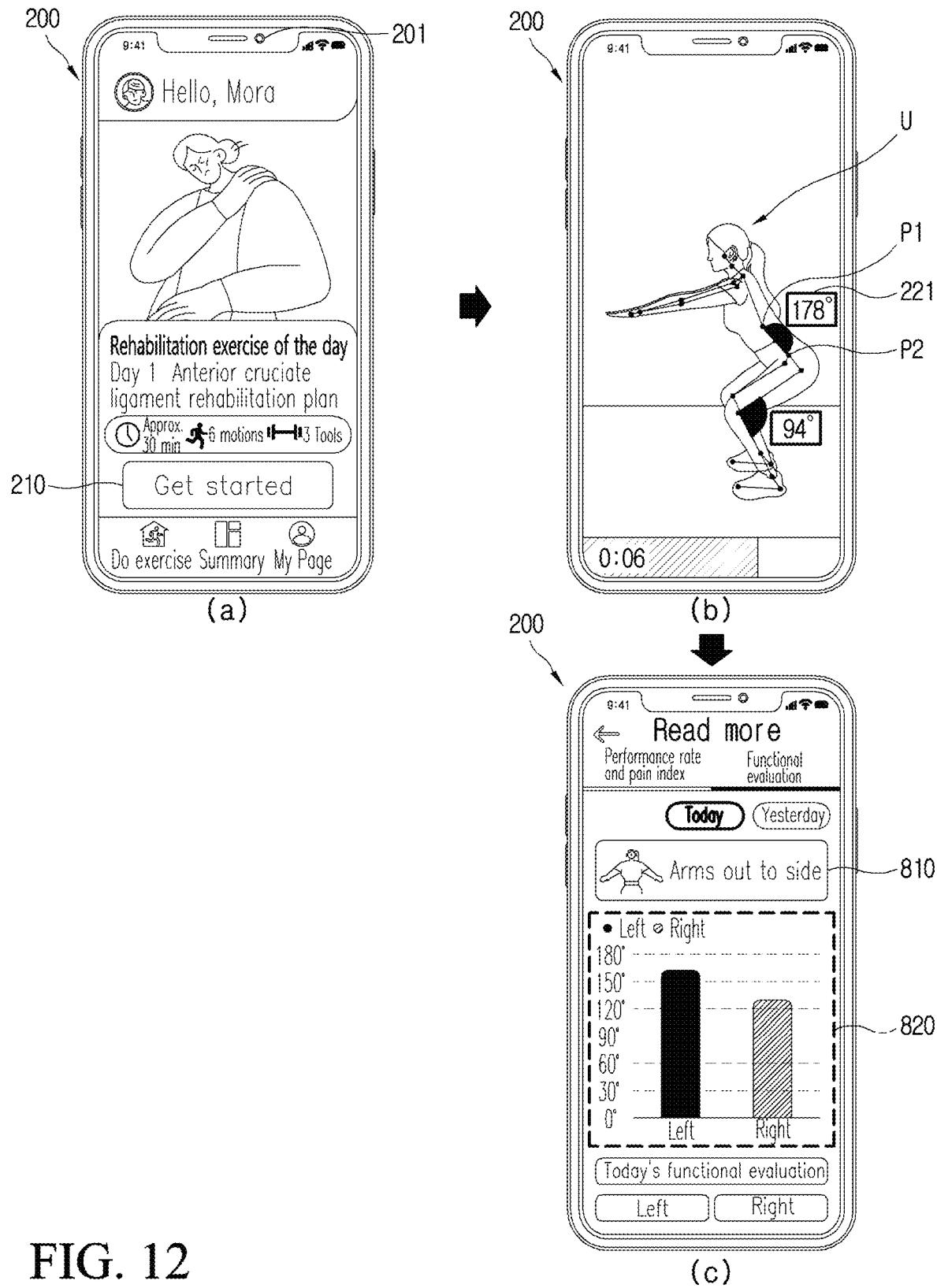
FIGS. 12 and 13 are conceptual views for describing an application example that provides a motion analysis result of a user.

For example, as illustrated in (a) of FIG. 12, the service server 130 may, based on a graphical object 210 corresponding to "start an exercise" being selected from the user terminal 200, control a camera 201 provided on the user terminal 200 to be in an active state such that the camera 201 photographs an exercise image targeted for analysis. Further, the service server 130 may receive the exercise image targeted for analysis that is photographed by the camera 201 from the user terminal 200 in real time or based on the completion of the user's exercise.

As illustrated in (b) of FIG. 12, the service server 130 may provide the exercise motion analysis result using the analysis result to the user terminal 200 on the basis of the completion of the analysis of the exercise motion of the user included in the image to be analyzed based on the posture estimation model 122. The exercise motion analysis result provided to the user terminal 200 by the service server 130 may include a variety of information. For example, the service server 130 may render the graphic objects corresponding to the joint points P1 and P2 to the subject U corresponding to the user and provide them on the user terminal 200. In this case, the service server 130 may provide the joint range of motion information (angle information, 221) of the subject U together.

Further, as illustrated in (c) of FIG. 12, the service server 130 may provide, on the user terminal 200, a plurality of exercise posture information 820 for each joint point of the subject U performing a specific exercise posture (e.g., "arms out to side", 810). For example, the service server 130 may provide, on the user terminal 200, a graph of a range of motion of a joint for a joint point positioned on a first side (e.g., left) of the user and a range of motion of a joint for a joint point positioned on a second side (e.g., right) of the patient.

Meanwhile, the service server 130 may, based on a motion analysis result for a specific exercise motion of the user, prescribe (provide) an exercise plan (or exercise program) including at least one exercise motion to the user.

Figure 13:
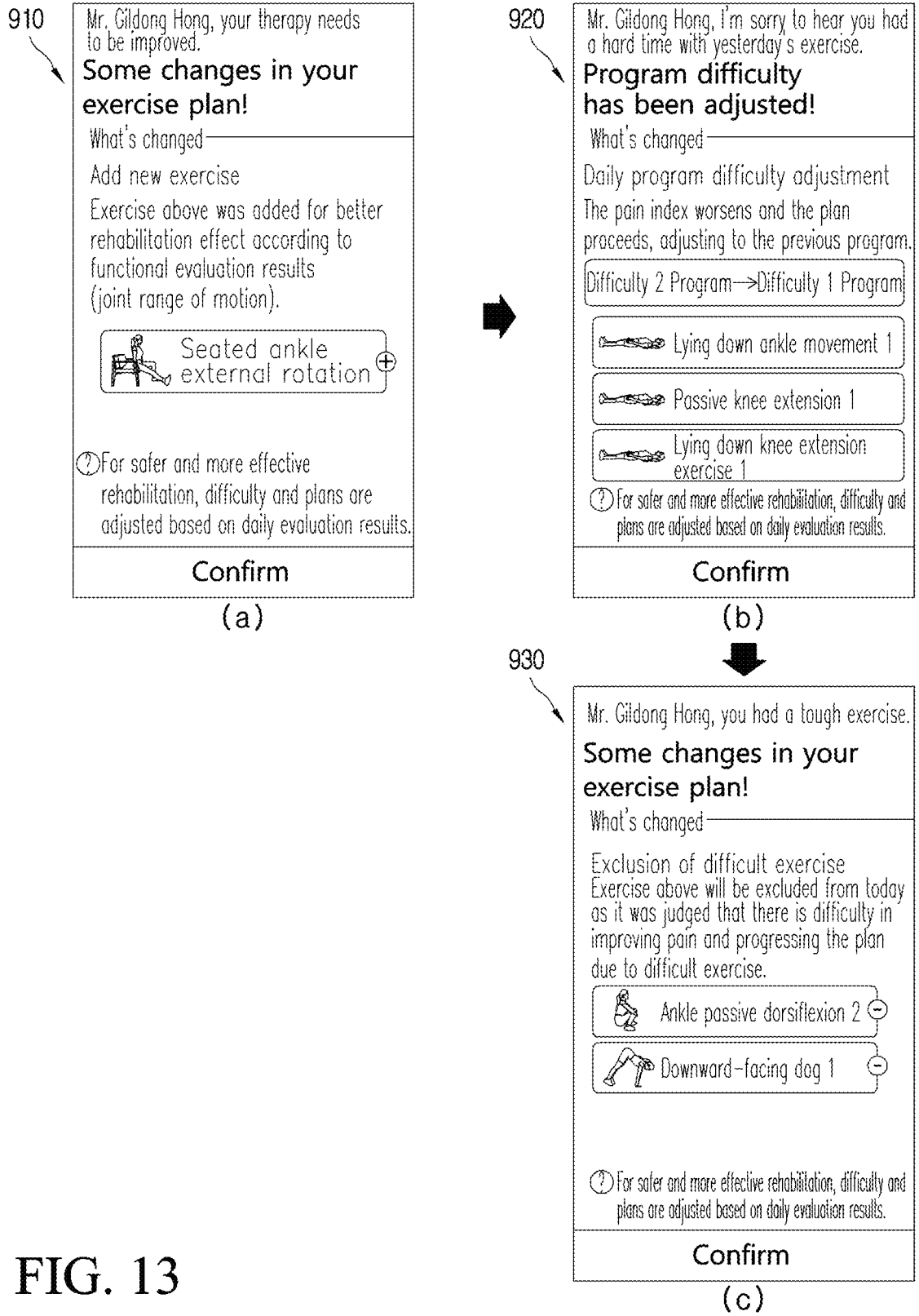

For example, as illustrated in (a) of FIG. 13, the service server 130 may, based on the exercise motion analysis result, add an exercise motion to an exercise plan (or exercise program) and provide, on the user terminal 200, a service page 910 that includes information on the exercise plan (or exercise program) including the added exercise motion.

In another example, as illustrated in (b) of FIG. 13, the service server 130 may, based on the motion analysis posture result, adjust the difficulty level of an exercise plan (or exercise program) and provide, on the user terminal 200, a service page 920 that includes information on the adjusted difficulty level.

In yet another example, as illustrated in (c) of FIG. 13, the service server 130 may, based on the exercise motion analysis result, exclude a portion of an exercise motion from an exercise plan (or exercise program) and provide, on the user terminal 200, a service page 930 guiding that the exercise motion has been excluded.

As described above, the system for estimating exercise posture and analyzing an exercise motion according to the present invention can analyze an exercise motion related to a specific exercise motion of a user included in an exercise image based on a posture estimation model and a motion analysis model (or a motion analysis unit) trained using a training data set including position information for a joint point. Therefore, in the present invention, it is possible to accurately analyze posture of a user from an exercise image, and in particular, it is possible to improve the quality of healthcare services by obtaining information on a range of motion, alignment state, and deviation state of a joint of the user.

Further, the method and system for estimating exercise posture according to the present invention can provide an exercise motion analysis result of a user related to a specific exercise motion to the user terminal, so that a patient can be provided with rehabilitation therapy without having to visit a hospital located at a distance, thereby making rehabilitation therapy easily accessible, and a healthcare provider can conveniently monitor a rehabilitation exercise of the patient through an electronic device, and provide feedback based on the monitoring, thereby enhancing an effect of exercise therapy of the patient.

As described above, the method and system for providing exercise therapy using an artificial intelligence posture estimation model and motion analysis model, according to the present invention, can receive, from a doctor terminal, prescription information related to an exercise for a patient, and, based on the prescription information, allocate an exercise plan including at least one prescribed exercise to an account of the patient. This allows a doctor to prescribe to a patient, and a patient to be provided with an exercise plan based on the doctor's prescription, even if the doctor and patient do not meet in person for exercise therapy for a musculoskeletal disease, thereby resolving spatial, temporal, and economic constraints on the exercise therapy and increasing accessibility to the exercise therapy.

Further, the method and system for providing exercise therapy using an artificial intelligence posture estimation model and motion analysis model, according to the present invention, can analyze an exercise motion of a user by extracting a keypoint corresponding to each of a plurality of preset joint points from an exercise image to focus on a joint required for exercise therapy of a musculoskeletal disease.

Further, the method and system for providing exercise therapy using an artificial intelligence posture estimation model and motion analysis model, according to the present invention, can analyze an exercise motion related to a specific exercise motion of a user included in an exercise image based on a posture estimation model trained using a training data set including position information for a joint point. Therefore, in the present invention, it is possible to accurately analyze posture of a patient from an exercise image, and in particular, it is possible to improve the quality of healthcare services by obtaining information on a range of motion, alignment state, and deviation state of a joint of the patient.

Further, the method and system for providing exercise therapy using an artificial intelligence posture estimation model and motion analysis model, according to the present invention, by transmitting an analysis result of an exercise motion of a patient to a patient terminal, the patient can be provided with feedback on an exercise image without having to visit a hospital located at a distance, thereby enhancing an effect of exercise therapy.

Meanwhile, the present invention described above may be executed by one or more processes on a computer and implemented as a program that can be stored on a computer-readable medium (or recording medium).

Further, the present invention described above may be implemented as computer-readable code or instructions on a medium in which a program is recorded. That is, the present invention may be provided in the form of a program.

Meanwhile, the computer-readable medium includes all kinds of storage devices for storing data readable by a computer system. Examples of computer-readable media include hard disk drives (HDDs), solid state disks (SSDs), silicon disk drives (SDDs), ROMs, RAMs, CD-ROMs, magnetic tapes, floppy discs, and optical data storage devices.

Further, the computer-readable medium may be a server or cloud storage that includes storage and that the electronic device is accessible through communication. In this case, the computer may download the program according to the present invention from the server or cloud storage, through wired or wireless communication.

Further, in the present invention, the computer described above is an electronic device equipped with a processor, that is, a central processing unit (CPU), and is not particularly limited to any type.

Meanwhile, it should be appreciated that the detailed description is interpreted as being illustrative in every sense, not restrictive. The scope of the present invention should be determined based on the reasonable interpretation of the appended claims, and all of the modifications within the equivalent scope of the present invention belong to the scope of the present invention.

What is claimed is:

1. A method of providing an exercise therapy using an artificial intelligence motion analysis model, the method comprising:
   receiving, from a doctor terminal, prescription information related to an exercise for a patient;
   allocating, to an account of the patient, based on the prescription information, an exercise plan including a prescribed exercise;
   receiving, from a patient terminal, an exercise image of the prescribed exercise;
   extracting, from the exercise image including a subject of the patient, keypoints corresponding to a plurality of preset joint points, using an artificial intelligence posture estimation model trained based on a training data set;
   analyzing, using an artificial intelligence motion analysis model, a relative positional relationship between the keypoints, and analyzing, based on the relative positional relationship, an exercise motion of the patient for the prescribed exercise; and
   transmitting an analysis result of the exercise motion of the patient to the patient terminal,
   wherein the artificial intelligence posture estimation model, trained with the training data set, extracts each of visible joint points and invisible joint points of the subject from the exercise image as the keypoints, such that the artificial intelligence motion analysis model analyzes the exercise motion of the patient based on all of the visible joint points that are visible and the invisible joint points that are invisible in the exercise image,
   wherein the training data set from which the artificial intelligence posture estimation model is trained is configured with a plurality of data groups, each corresponding to a different information attribute,
   wherein, in a first data group of the plurality of data groups, position information of predesignated plurality of training target joint points among the visible joint points and the invisible joint points of the subject included in a training target exercise image is sequentially arranged based on a predefined sequence corresponding to each of the predesignated plurality of training target joint points,
   wherein, in a second data group of the plurality of data groups, a data value representing whether each of the predesignated plurality of training target joint points is visible in the training target exercise image is arranged in a same sequence as the position information included in the first data group,
   wherein position information arranged in a specific sequence in the first data group is defined as position information of one of a first type and a second type different from the first type based on a data value arranged in the specific sequence in the second data group, wherein the first type of position information is actual position information on an area where the predesignated plurality of training target joint point is actually positioned in the training target exercise image, wherein the second type of position information is predicted position information on the predesignated plurality of training target joint point predicted from the training target exercise image, and wherein the artificial intelligence posture estimation model, based on the data value arranged in the specific sequence of the second data group, differently sets a training weight for the position information arranged in the specific sequence of the first data group.

2. The method of claim 1, further comprising:

outputting the exercise image to the patient terminal in real time, in conjunction with the exercise image being photographed on the patient terminal; and providing a graphic object corresponding to an extracted keypoint that overlaps an area where a subject corresponding to the patient is positioned in the exercise image, so as to allow the patient to recognize a joint point where an analysis is performed on an exercise posture of the patient.

3. The method of claim 2, wherein in the extracting keypoints, the visible joint points are specified among the plurality of preset joint points, and the invisible joint points are predicted among the plurality of preset joint points.

4. The method of claim 2, wherein in the analyzing the exercise motion of the patient, a relative positional relationship between the keypoints is analyzed based on rule information related to the prescribed exercise, and the exercise motion of the patient is analyzed by judging whether the relative positional relationship between the keypoints satisfies the rule information.

5. The method of claim 4, wherein visual appearances of graphic objects overlapping the exercise image are different depending on whether the relative positional relationship between extracted keypoints satisfies the rule information.

6. The method of claim 5, wherein the analysis result of the exercise motion of the patient includes:

a first analysis result providing the graphic object corresponding to the extracted keypoint that overlaps the exercise image in real time with a different visual appearance based on the rule information, in a state in which the exercise image is being photographed on the patient terminal; and a second analysis result including an evaluation score of the patient for the prescribed exercise based on a keypoint extracted from each of a plurality of frames constituting the exercise image, wherein the first analysis result is generated by a motion analysis model of an application installed on the patient terminal, wherein the second analysis result is generated on a cloud server in conjunction with the application, and wherein both the first analysis result and the second analysis result are transmitted to the doctor terminal.

7. A system for providing an exercise therapy, the system comprising:

a communication unit configured to receive, from a doctor terminal, prescription information related to an exercise for a patient; and a control unit configured to allocate, to an account of the patient, based on the prescription information, an exercise plan including a prescribed exercise, wherein the control unit is configured to:

receive, from a patient terminal, an exercise image of the prescribed exercise;

extract, from the exercise image including a subject of the patient, keypoints corresponding to a plurality of preset joint points, using an artificial intelligence posture estimation model trained based on a training data set;

analyze, using an artificial intelligence motion analysis model, a relative positional relationship between the keypoints, and analyzing, based on the relative positional relationship, an exercise motion of the patient for the prescribed exercise; and transmit an analysis result of the exercise motion of the patient to the patient terminal, wherein the artificial intelligence posture estimation model, trained with the training data set, extracts each of visible joint points and invisible joint points of the subject from the exercise image as the keypoints, such that the artificial intelligence motion analysis model analyzes the exercise motion of the patient based on all of the visible joint points that are visible and the invisible joint points that are invisible in the exercise image, wherein the training data set from which the artificial intelligence posture estimation model is trained is configured with a plurality of data groups, each corresponding to a different information attribute, wherein, in a first data group of the plurality of data groups, position information of predesignated plurality of training target joint points among the visible joint points and the invisible joint points of the subject included in a training target exercise image is sequentially arranged based on a predefined sequence corresponding to each of the predesignated plurality of training target joint points, wherein, in a second data group of the plurality of data groups, a data value representing whether each of the predesignated plurality of training target joint points is visible in the training target exercise image is arranged in a same sequence as the position information included in the first data group, wherein position information arranged in a specific sequence in the first data group is defined as position information of one of a first type and a second type different from the first type based on a data value arranged in the specific sequence in the second data group, wherein the first type of position information is actual position information on an area where the predesignated plurality of training target joint point is actually positioned in the training target exercise image, wherein the second type of position information is predicted position information on the predesignated plurality of training target joint point predicted from the training target exercise image, and wherein the artificial intelligence posture estimation model, based on the data value arranged in the specific sequence of the second data group, differently sets a training weight for the position information arranged in the specific sequence of the first data group.

8. A program executable by at least one processor of an electronic device and stored on a non-transitory computer-readable recording medium of the electronic device, the program, when executed by the at least one processor, to perform steps of:

receiving, from a doctor terminal, prescription information related to an exercise for a patient;

allocating, to an account of the patient, based on the prescription information, an exercise plan including a prescribed exercise;

receiving, from a patient terminal, an exercise image of the prescribed exercise;

extracting, from the exercise image including a subject of the patient, keypoints corresponding to a plurality of preset joint points, using an artificial intelligence posture estimation model trained based on a training data set;

analyzing, using an artificial intelligence motion analysis model, a relative positional relationship between the keypoints, and analyzing, based on the relative positional relationship, an exercise motion of the patient for the prescribed exercise; and transmitting an analysis result of the exercise motion of the patient to the patient terminal, wherein the artificial intelligence posture estimation model, trained with the training data set, extracts each of visible joint points and invisible joint points of the subject from the exercise image as the keypoints, such that the artificial intelligence motion analysis model analyzes the exercise motion of the patient based on all of the visible joint points that are visible and the invisible joint points that are invisible in the exercise image, wherein the training data set from which the artificial intelligence posture estimation model is trained is configured with a plurality of data groups, each corresponding to a different information attribute, wherein, in a first data group of the plurality of data groups, position information of predesignated plurality of training target joint points among the visible joint points and the invisible joint points of the subject included in a training target exercise image is sequentially arranged based on a predefined sequence corresponding to each of the predesignated plurality of training target joint points, wherein, in a second data group of the plurality of data groups, a data value representing whether each of the predesignated plurality of training target joint points is visible in the training target exercise image is arranged in a same sequence as the position information included in the first data group, wherein position information arranged in a specific sequence in the first data group is defined as position information of one of a first type and a second type different from the first type based on a data value arranged in the specific sequence in the second data group, wherein the first type of position information is actual position information on an area where the predesignated plurality of training target joint point is actually positioned in the training target exercise image, wherein the second type of position information is predicted position information on the predesignated plurality of training target joint point predicted from the training target exercise image, and wherein the artificial intelligence posture estimation model, based on the data value arranged in the specific sequence of the second data group, differently sets a training weight for the position information arranged in the specific sequence of the first data group.

* * * * *